US010676492B2

United States Patent
Jaffrès et al.

(10) Patent No.: US 10,676,492 B2
(45) Date of Patent: Jun. 9, 2020

(54) BRANCHED AMPHIPHILIC LIPIDS

(71) Applicants: UNIVERSITÉ DE BRETAGNE OCCIDENTALE, Brest (FR); INSERM (INSTITUT NATIONAL DE LA SANTÉ ET DE LA RECHERCHE MÉDICALE, Paris (FR); CENTRE HOSPITALIER RÉGIONAL ET UNIVERSITAIRE DE BREST, Brest (FR)

(72) Inventors: Paul-Alain Jaffrès, Bohars (FR); Hélène Couthon-Courvès, Bohars (FR); Damien Afonso, Brest (FR); Tristan Montier, Brest (FR); Tony Le Gall, Brest (FR)

(73) Assignees: UNIVERSITÉ DE BRETAGNE OCCIDENTALE, Brest (FR); INSERM (INSTITUT NATIONAL DE LA SANTÉ ET DE LA RECHERCHE MÉDICALE), Paris (FR); CENTRE HOSPITALIER RÉGIONAL ET UNIVERSITAIRE DE BREST, Brest (FR)

( * ) Notice: Subject to any disclaimer, the term of this patent is extended or adjusted under 35 U.S.C. 154(b) by 0 days.

(21) Appl. No.: 15/761,350

(22) PCT Filed: Sep. 23, 2016

(86) PCT No.: PCT/FR2016/052410
§ 371 (c)(1),
(2) Date: Mar. 19, 2018

(87) PCT Pub. No.: WO2017/051129
PCT Pub. Date: Mar. 30, 2017

(65) Prior Publication Data
US 2018/0265528 A1 Sep. 20, 2018

(30) Foreign Application Priority Data

Sep. 25, 2015 (FR) .................... 15 59066

(51) Int. Cl.
*C07C 217/28* (2006.01)
*C07F 9/24* (2006.01)
*A61K 9/127* (2006.01)
*C12N 15/88* (2006.01)

(52) U.S. Cl.
CPC ............ *C07F 9/2458* (2013.01); *A61K 9/127* (2013.01); *C07C 217/28* (2013.01); *C12N 15/88* (2013.01)

(58) Field of Classification Search
None
See application file for complete search history.

(56) References Cited

U.S. PATENT DOCUMENTS 3,041,284 A 6/1962 Calhoun et al.

FOREIGN PATENT DOCUMENTS

CN 103333169 2/2014

OTHER PUBLICATIONS

Felgner et al, "Lipofection: a highly efficient, lipid-mediated DNA-transfection procedure", Proceedings of the National Academy of Sciences of the United States of America, 1987, vol. 84, No. 21, pp. 7413-7417.
Ewert et al, "Cationic Lipid-DNA Complexes for Gene Therapy: Understanding the Relationship Between Complex Structure and Gene Delivery Pathways at the Molecular Level" Current Medicinal Chemistry, 2004, vol. 11, No. 2, pp. 133-149.
Dan et al, "Structure and kinetics of lipid-nucleic acid complexes" Advances in Colloid and Interface Science, 2014, vol. 205, pp. 230-239.
Ewert et al, "A Columnar Phase of Dendritic Lipid-Based Cationic Liposome—DNA Complexes for Gene Delivery: Hexagonally Ordered Cylindrical Micelles Embedded in a DNA Honeycomb Lattice" Journal of the American Chemical Society, 2006, vol. 128, No. 12, pp. 3998-4006.
Lindberg M. et al., "The gene transfection properties of a lipophosphoramidate derivative with two phytanyl chains", Biomaterials, 2012, vol. 33, No. 26, pp. 6240-6253.

(Continued)

*Primary Examiner* — Ana Z Muresan
(74) *Attorney, Agent, or Firm* — Young & Thompson

(57) ABSTRACT

Disclosed are novel branched amphiphilic lipids, in particular novel branched amphiphilic lipids of general formula (II). Also disclosed is a method of synthesis for the compounds of formula (II), from unsaturated amphiphilic compounds of general formula (I). Further disclosed is the use of the compounds of general formula (II) and of the lipoplexes obtained by formulation of the compounds of general formula (II) for applications, particularly transfection, in which improved fusion properties are desired.

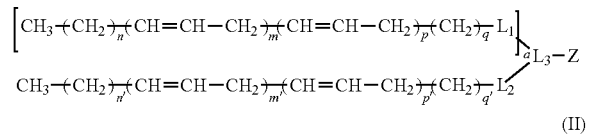

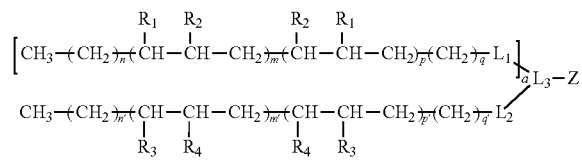

9 Claims, 5 Drawing Sheets

(56) References Cited

OTHER PUBLICATIONS

Le Corre et al, "Cationic lipophosphoramidates with two different lipid chains: synthesis and evaluation as gene carriers" Organic Biomolecular Chemistry, 2014, vol. 12, pp. 1463-1474 (protocole).
Massiot et al, "Modelling one- and two-dimensional solid-state NMR spectra" Magnetic Resonance in Chemistry, 2002, vol. 40, pp. 70-76 (protocole).
Le Gall et al, "A Novel Cationic Lipophosphoramide with Diunsaturated Lipid Chains: Synthesis, Physicochemical Properties, and Transfection Activities" Journal of Medicinal Chemistry 2010, vol. 53, No. 4, pp. 1496-1508 (protocole).
Javier Munoz F et al., "Glycan Tagging to Produce bioactive ligands for a surface Plasmon resonance (SPR) Study via immobilization on different surfaces" ,Bioconjugate Chemistry, 2009, vol. 20, pp. 673-682.
More et al., "AB type polyaddition route to thermoplastic polyurethanes from fatty acid derivatives", Polymer Chemistry, 2012, vol. 3, No. 6, pp. 1594-1605.
Mamedov S et al., "Synthesis and reactions of aziridine derivatives of sulfonamides and their study as additives for lubricating oils", Neftekhimiya, 2009, vol. 49, No. 3, pp. 272-277.

BRANCHED AMPHIPHILIC LIPIDS

FIELD OF THE INVENTION

The present invention relates to novel branched amphiphilic lipids. In particular, this invention relates to novel branched amphiphilic lipids of general formula (II). This invention also proposes a method of synthesis for said compounds of formula (II), from unsaturated amphiphilic compounds of general formula (I). This invention also relates to the use of the compounds of general formula (II) and of lipoplexes obtained by formulation of the compounds of general formula (II) for applications, particularly transfection, in which improved fusion properties are desired.

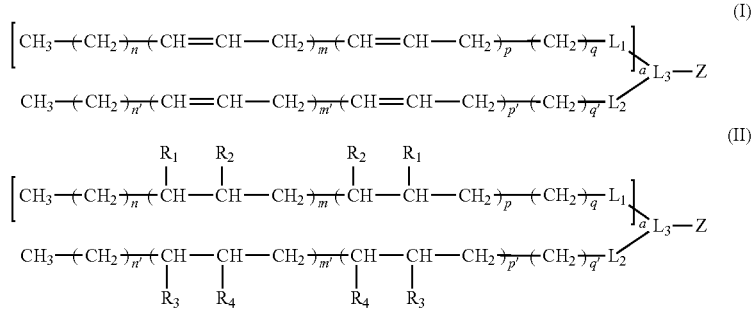

BACKGROUND OF INVENTION

Cationic amphiphilic lipids constituent a vast class of vectors commonly used for the vectorisation of nucleic acids (pDNA, siRNA, mRNA) in vitro or in vivo.

Since the pioneering work of Felgner et al. (Felgner, P. L. G.; Gadek, T. R.; Holm, M.; Roman, R.; Chan, H. W.; Wenz, M.; Northrop, J. P.; Ringold, M. G.; Danielsen, M. *Proc. Natl. Acad. Sci. U.S.A.*, 1987, 84, 7413-7417), efforts have been made to propose novel structures of cationic amphiphilic lipids that make it possible to improve the effectiveness of the transfection and to expand the knowledge of transfection mechanisms.

Transfection is carried out thanks to supramolecular aggregates formed by the association of a cationic amphiphilic lipid with DNA (lipoplexes). After the cellular internalisation of these lipoplexes which is produced by endocytosis pathway, the release of the nucleic material from the endosomes to the cytosol is necessary in order to prevent degradation of the loaded material inside the lysosomes.

Different strategies based on a molecular approach have been explored to promote the destabilisation of the endosomal membrane or act on the stability of lipoplexes after the cellular internalization thereof.

As such novel cationic amphiphilic lipids that can be protonated in the endosomes (proton sponge effect) or cleaved by an enzymatic or redox reaction in the cytosol have been proposed to destabilise the endosomal membrane.

Another strategy for improving the efficiency of transfection consists in improving the stability and the fusion properties of lipoplexes (a) Ewert, K.; Slack, N. L.; Ahmad, A.; Evans, H. M.; Lin, A. J.; Samuel, C. E.; Safinya, C. R. *Curr Med Chem.*, 2004, 11, 133-49; b) Dan, N.; Danino, D. *Adv Colloid Interface Sci.*, 2014, 205, 230-9). Work in particular has provided an improvement in transfections by associating co-lipids such as 1,2-dioleoyl-sn-glycero-3-phosphoetanolamine (DOPE) with a cationic amphiphilic lipid. This improvement is attributed to the propensity of DOPE to adopt a reversed hexagonal phase which is known to be more fusogenic than the lamellar phases.

Another strategy for producing non-lamellar phase consists in acting on the molecular form of cationic amphiphilic lipids. Ewert et al. reported the synthesis of cationic amphiphilic lipids having a dendretic head group (Ewert, K. K.; Evans, H. M.; Zidovska, A.; Bouxsein N. F.; Ahmad, A.; Safinya, C. R. *J. Am. Chem. Soc.* 2006, 128, 3998-4006). The shape of this cationic polar head induced the formation of hexagonal phases $H_I$ when they are included in a binary formulation. High transfection efficiencies were observed on cell lines known to be difficult to transfect. Lindberg et al have shown that the incorporation of two phytanyl chains (methylated C16-alkyl chains) into the cationic lipo-phosphoramidate structure produces a reversed hexagonal phase after the formulation in water (Lindberg, M.; Carmoy, N.; Le Gall, T.; Fraix, A.; Berchel, M.; Lorilleux, C.; Couthon-Gourvès, H.; Bellaud, P.; Fautrel, A.; Jaffrès, P. A.; Lehn, P.; Montier, T. *Biomaterials* 2012, 33, 6240-6253). Good in vivo transfection efficiencies were obtained with this vector.

Despite all this work there is still a need for developing novel vectors.

It is also desirable that these novel amphiphilic lipids be obtained by synthesis routes optimised for large-scale production required for in vivo experiments. However, there is still a need for developing a novel method of synthesis making it possible to obtain novel branched amphiphilic lipids from a simple modification of the existing amphiphilic lipid structures, allowing a high modularity and not involving a synthesis de novo, i.e. completely synthesizing the desired molecule.

Definitions

In this invention, the terms hereinbelow are defined in the following way:

"imaging agent": relates to a compound that has the capacity to view an anatomical or pathological structure.

"alkenyl" relates to any linear or branched hydrocarbon chain, carrying at least one double bond, from 2 to 12 carbon atoms, preferably from 2 to 6 carbon atoms; such as for example ethenyl, 2-propenyl, 2-butenyl, 3-butenyl, 2-pentenyl and the isomers thereof, 2-hexenyl and the isomers thereof, 2,4-pentadienyl.

"alkynyl": relates to any branched or unbranched hydrocarbon chain, carrying at least one triple bond, from 2 to 12 carbon atoms, preferably from 2 to 6 carbon atoms, such as for example ethynyl, 2-propynyl, 2-butynyl, 3-butynyl, 2-pentynyl and the isomers thereof, 2-hexynyl and the isomers thereof "acylamino": relates to the —NRC(O)alkyl, —NRC(O)cycloalkyl, —NRC(O)cycloalkenyl, —NRC(O)alkenyl, —NRC(O)alkynyl, —NRC(O)aryl, —NRC(O)heteroaryl and —NRC(O)heterocyclic groups, wherein R is a hydrogen or an alkyl such as defined hereinbelow.

"alkyl": relates to any saturated linear or branched hydrocarbon chain, from 1 to 12 carbon atoms, preferably from 1 to 6 carbon atoms, such as for example methyl, ethyl, n-propyl, isopropyl, n-butyl, sec-butyl, isobutyl, tertio-butyl, pentyl and the isomers thereof (e.g. n-pentyl, iso-pentyl), hexyl and the isomers thereof (e.g. n-hexyl, iso-hexyl), and even more preferably from 1 to 3 carbons, such as for example methyl, ethyl, n-propyl, isopropyl.

"alkyl amino": relates to the —NHR group wherein R is an alkyl such as defined hereinabove.

"alkylaryl": relates to a group comprising an aryl group such as defined hereinabove covalently bonded to an alkyl group such as defined hereinabove and connected by the aryl group.

"alkyloxy": relates to any —O-alkyl group.

"alkyloxycarbonyl": relates to any —C(O)—O-alkyl group.

"amine": relates to the —NH$_2$ group.

"aminocarbonyl": relates to the —C(O)NR'R" groups wherein R' and R" independently chosen from the group comprising hydrogen, alkyl, alkenyl, alkynyl, aryl, cycloalkyl, cycloalkenyl, heteroaryl and heterocyclic, and wherein R' and R" are optionally connected together with the nitrogen to which they are linked in order to form a heterocyclic or substituted heterocyclic group, such as for example a substituted piperazine.

"aminothiocarbonyl": relates to the —C(S)NR'R" groups wherein R' and R" independently chosen from the group comprising hydrogen, alkyl, alkenyl, alkynyl, aryl, cycloalkyl, cycloalkenyl, heteroaryl and heterocyclic, and wherein R' and R" are optionally connected together with the nitrogen to which they are linked in order to form a heterocyclic or substituted heterocyclic group, such as for example a substituted piperazine.

"amphiphilic": relates to a chemical species having both at least one hydrophilic group and at least one hydrophobic group. Triglycerides are not amphiphilic species; According to an embodiment of the invention, the compounds of formula (II) are not triglycerides.

"aryl": relates to a mono- or polycyclic system of 5 to 20, preferably from 6 to 12, carbon atoms that have one or several aromatic rings (when there are two cores, reference is made to a biaryl) among which can be mentioned the phenyl group, the biphenyl group, the 1-naphtyl group, the 2-naphtyl group, the tetrahydronaphtyl group, the indanyl group, and the binaphtyl group.

"arylalkyl": relates to a group comprising an alkyl group such as defined hereinabove covalently bonded to an aryl group such as defined hereinabove and connected by the alkyl group.

"counterion": relates to a mobile ion of the opposite sign. Non-limiting examples of these counterions include ions of alkali metals, alkaline earth metals, transition metals, ammonium, pyridinium, chloride, bromide, iodide, tosylates, triflates, methylsulphate.

"cycloalkyl": relates to a cyclic or polycyclic alkyl group, comprising from 3 to 8 carbon atoms; preferably a cyclopropyl, cyclopentyl or cyclohexyl group.

"cycloalkenyl": relates to a cyclic or polycyclic alkenyl group, comprising from 3 to 8 carbon atoms; preferably a cyclopropeneyl, cyclopenteneyl or cyclohexeneyl group.

"dialkylamino": relates to the —NRR' group wherein R and R' are alkyls such as defined hereinabove.

"heterocycle": relates to a non-aromatic group, fully saturated or partially unsaturated (for example, a cyclic compound comprising from 3 to 7 atoms, a bicyclic compound having 7 to 11 carbon atoms) having at least one heteroatom on one of the carbon rings. Each ring of the heterocycle group containing a heteroatom can have 1, 2, 3 or 4 heteroatoms selected from nitrogen, oxygen and/or sulphur, the sulphur and nitrogen atoms can optionally be oxidised and the nitrogen atom potentially quaternary. The heterocyclic group can be attached to any heteroatom or carbon atom of the ring, where valency so allows. The rings of the polycyclic heterocycles can be fused, bridged and/or connected by one or several spiro atoms. Non-limiting examples of these rings include the aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl groups.

"heteroaryl": relates to but is not limited to aromatic rings from 5 to 12 carbon atoms which are fused or covalently bonded, typically containing 5 to 6 atoms; at least one of the aromatic carbons in at least one of the rings is replaced with oxygen, nitrogen or sulphur, the nitrogen and the sulphur can potentially be oxidised and the nitrogen potentially in quaternary form. Such rings can be fused with an aryl, cycloalkyl, heteroaryl or heterocyclyl. Non-limiting examples of these rings include the pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo [2,1-b] [1,3] thiazolyl, thieno [3,2-b] furanyl, thieno [3,2-b] thiophenyl, thieno [2,3-d] [1,3] thiazolyl, thieno [2,3-d] imidazolyl, tetrazolo [1,5-a] pyridinyl, indolyl, indolizinyl, iso-indolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo [1,2-a] pyridinyl, a 6-oxo-pyridazine-1(6H)-yl, 2-oxo-pyridine-1(2H)-yl, 6-oxo-pyrudazin-1(6H)-yl, 2-oxo-pyridine-1(2H)-yl, 1,3-benzodioxolyl, quinolinyl, isoquinolinyl, cinnolinyl, quinazolinyl, quinoxalinyl groups.

"protonable neutral heterocycle": relates to but is not limited to aromatic rings of 5 to 12 carbon atoms which are fused or covalently bonded, typically containing 5 to 6 atoms; at least one of the aromatic carbons in at least one of the cycles is replaced with nitrogen and is able to be protonated. Non-limiting examples of these rings include the imidazole, pyridine, pyridazine, pyrimidine, pyrazine, quinoleine, quinoxaline, indole groups.

"polar group": relates to a hydrophilic group.

"reactive group": relates to a group capable of reacting with another chemical group to form a covalent bond, i.e. covalently reactive under suitable reaction conditions, and are generally a point of attachment for another substance. The reactive group is a group present on the compounds of this invention which is capable of chemically reacting with a functional group on a different compound in order to form a covalent bond. The reactive groups include in general the nucleophilic groups, electrophilic groups and the photoactivated groups.

"halo": relates to the fluoro, chloro, bromo, or iodo groups.

"halogen": relates to the atoms of fluorine, chlorine, bromine and iodine, preferably relates to the atoms of chlorine, bromine and iodine.

"linker" or "bonding group": refers to a covalent bond or a group comprising a series of stable covalent bonds, with the group comprising from 1 to 40 multivalent atoms chosen from the group comprising C, N, O, S and P; covalently bonding a group, a coupling function or a vectoring group to the rest of the ligand of the invention. The number of multivalent atoms in a linker can be, for example, 0, 1, 2, 3, 4, 5, 6, 7, 8, 9, 10, 20, 25 or 30. A linker can be linear or non-linear; certain linkers have side chains or pendant functional groups (or both). Examples of such side chains are hydrophilicity modifiers, for example solubilising groups such as, for example, sulfo (—SO3H or —SO3-) or carboxylate (—COO—). In an embodiment, a linker is comprised of any combination of carbon-carbon, carbon-nitrogen, nitrogen-nitrogen, carbon-oxygen and carbon-sulphur single, double, triple or aromatic bonds. The linkers may for example consist of a combination of groups chosen from the alkyl, —C(O)NH—, —C(O)O—, —NH—, —S—, —O—, —C(O)—, —S(O)n- groups wherein n is equal to 0, 1 or 2; monocyclic 5- or 6-membered rings and functional side chains (for example sulfo, hydroxy or carboxy). Furthermore, when the linker binds a coupling function to the remainder of the ligand of the invention, said coupling function can then be reacted with a reactive substance having vectorising functions, leading to a ligand wherein the linker binds a vectorising group to the rest of the ligand. In this case, the linker typically contains a residue of a coupling function (such as for example the carbonyl group of an ester, the triazolo group resulting from a click reaction between an azide and an alkyne, or the —NHC(=S)NH— group resulting from the coupling of an amine on an isothiocyanate function). According to an embodiment, the linker refers to a single covalent bond.

"lipid": relates to a saturated, unsaturated or polyunsaturated linear or branched carbon chain. This pattern can be attached to the structure of an amphiphilic by a functional group.

"lipoplex": relates to a nucleic acid-liposome complex; said nucleic acid can be DNA, siRNA or mRNA.

"liposome": relates to an artificial vesicle formed by concentric lipid bilayers, trapping therebetween aqueous compartments. The liposomes are obtained from amphiphilics.

the term "pharmaceutically acceptable" means that the ingredients of a pharmaceutical composition are compatible with each other and not deleterious to the patient.

"prodrug": relates to pharmaceutically acceptable derivatives, such as for example amides or esters, of which in vivo biotransformation product generates the biologically active compound. Prodrugs are generally characterised by increased bio-availability and are readily metabolised into biologically active compounds in vivo.

"organic salt": relates to an ionic compound comprised of cations and anions forming a neutral product and no net charge, with at least one of said ions being organic in nature, i.e. being a carbon compound; Non-limiting examples of these organic salts include ammonium, phosphonium, and imidazolium salts.

"transfection": relates to the introduction of exogenous genetic material into eukaryotic cells. Transfection may be carried out in vitro or in vivo.

"UV": relates to the portion of the electromagnetic spectrum from about 300 nm to about 400 nm.

"vehicle": relates to a substance that carries the product of interest in a composition, in particular this may be a substance that allows it to be dissolved. The vehicle can for example be water.

Phosphorus linkers are such as defined hereinbelow wherein R, R', R", R''', R'''' and R''''' are alkyls or alkylene such as defined hereinabove:

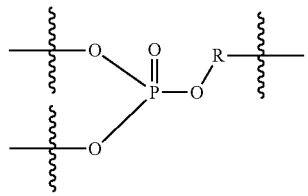

alkylphosphate

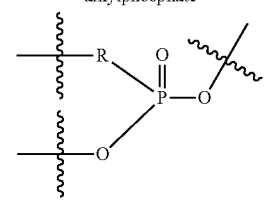

alkylphosphonate

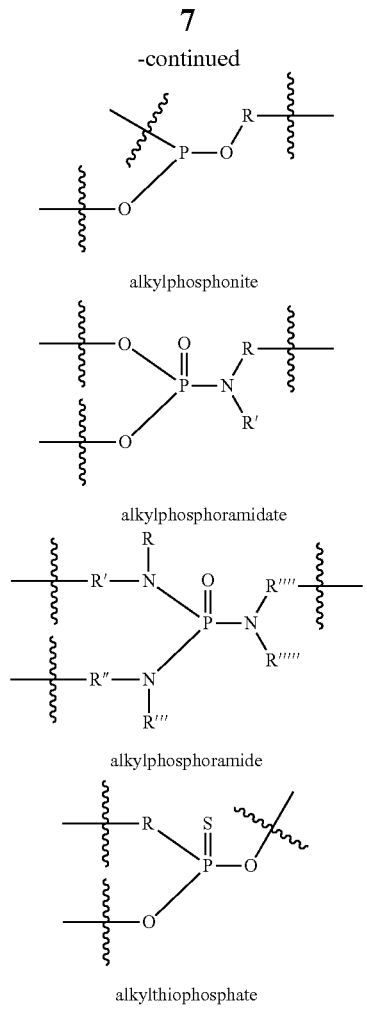

alkylphosphonite alkylphosphoramidate alkylphosphoramide alkylthiophosphate

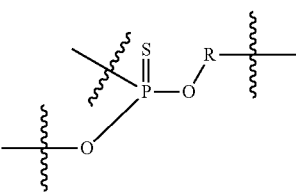

alkylthiophosphonate

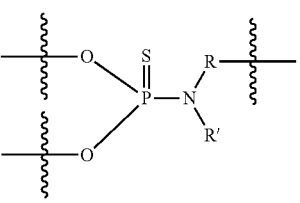

alkylthiophosphoramidate

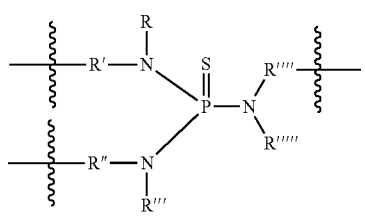

alkylthiophosphoramide

DETAILED DESCRIPTION

Compounds

This invention relates to an amphiphilic compound of general formula (II):

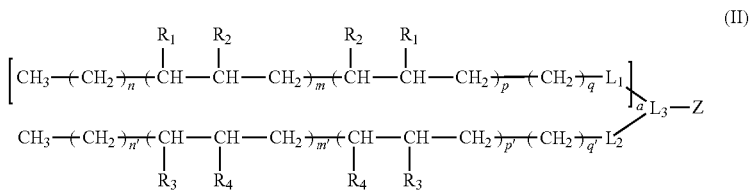

wherein:

L$_1$ and L$_2$ are each independently a linker, preferably the linker is chosen from a single bond and the alkyl, aryl, alkylaryl, arylalkyl, alkyloxy, or alkyloxycarbonyl groups;

L$_3$ is a linker, preferably the linker is chosen from the alkyl, alkylphosphoramidates, alkylthiophosphoramidates, alkylphosphate, alkylthiophosphate, alkylphosphonite, alkylphosphonate, alkylthiophosphonate, alkylphosphoramide, alkylthiophosphoramide, alkyloxy or amine groups; Z is a polar functional group, said group being cationic, anionic, zwitterionic or neutral;

a is 0 or 1;

n, n', q and q' are each independently an integer from 1 to 15;

m, m', p and p' are each independently an integer from 0 to 4 with the condition that:
at least one of m and p is different from 0;
at least one of m' and p' is different from 0;
$R_1$ and $R_2$ are one a hydrogen and the other a thioether group of formula —S-$L_4$-$R_5$ and $R_3$ and $R_4$ are one a hydrogen and the other a thioether group of formula —S-$L_4$-$R_5$ such that:
$L_4$ is a linker, preferably the linker is chosen from a single bond and the aminocarbonyl, acylamino, alkylaminocarbonyl, aminothiocarbonyl, alkyloxycarbonyl, alkyl, aryl, cycloalkyl, alkylaryl, arylalkyl, alkyloxy, polyethylene glycol (PEG), polypropylene glycol (PPG) groups, a peptide or a combination thereof; optionally interrupted or terminated by —O—, —S—, —SO$_2$— or a combination thereof; optionally further comprising a residue of a reactive group through which $L_4$ is connected to $R_5$;
$R_5$ is a hydrogen atom, or:
polar group chosen from the group of organic salts of the ammonium, phosphonium, and imidazolium type and protonable neutral heterocycles;
a reactive group chosen from the group comprising the group N3, amino, alkylamino, COOH, amide, maleimide, alkyne, SH, OH, ester, activated ester, activated carboxylic acid, halo, nitro, nitrile, isonitrile, acrylamide, aldehyde, ketone, acetals, ketals, anhydride, thiocyanate, isothiocyanate, isocyanate, hydrazine, hydrazides, hydrazones, ethers, oxides, cyanates, diazo, diazonium, sulphides, disulphides, sulphoxides, sulphones, sulphonic acids, sulphinic acids, sulphates, sulphenic acids, amidines, imides, imines, imidates, nitrones, hydroxylamines, oximes, hydroxamic acids thiohydroxamic acids, allenes, ortho esters, sulphites, enamines, ynamines, ureas, pseudo-ureas, semicarbazides, carbodiimides, and carbamates; or
a bioactive group selected from prodrugs, amino acids, peptides, proteins, antibodies, enzymes, polysaccharides, nucleosides, nucleotides, oligonucleotides, fluorophores, chromophores, radioisotopes, carboranes and combinations thereof
provided that when a is equal to 0 then Z is different from —S—CH2-CH2-OH and from —C(O)OMe.

The compound of the invention has the advantage of being functionalised or functionalisable. According to one embodiment, the functionalisation is carried out using $R_5$ when $R_5$ is a reactive group. According to an embodiment, the protonable neutral heterocycles are the imidazole and pyridine groups.

According to an embodiment, $L_1$ and $L_2$ are each independently a single bond or an alkyloxy group.

According to an embodiment, $L_3$ is a linker chosen from the alkyl, alkylphosphate, alkylphosphonate, alkylphosphoramidate, alkylthiophosphoramide, alkyloxy or amine groups. According to a preferred embodiment, $L_3$ is a alkylphosphoramidate group. According to another preferred embodiment, $L_3$ is an alkyloxy group.

According to an embodiment, $L_4$ is a linker, preferably the linker is chosen from a single bond and the alkyls, aryl, cycloalkyl, alkylaryl, arylalkyl, polyethylene glycol (PEG) and polypropylene glycol (PPG) groups. According to an embodiment, $L_4$ is a single bond or a linker, preferably the linker is chosen from the alkyl, cycloalkyl, aryl-alkyl groups. In these embodiments, $L_4$ is preferably chosen from the C1-C12 alkyl, cycloalkyl and aryl-alkyl groups. Preferably $L_4$ is chosen from the benzyl, cyclohexyl, propyl, hexyl, heptyl, undecyl and dodecyl groups.

According to an embodiment, $R_5$ is a hydrogen atom, a polar group chosen from the group of organic salts of the ammonium, phosphonium, and imidazolium type and protonable neutral heterocycles or a reactive group chosen from the group OH, carboxylic acid, amine, protected thiol function, azide, aldehyde, or a bioactive group chosen from prodrugs, fluorophores, chromophores, radioisotopes or carboranes. $R_5$ is preferably a hydrogen atom, an OH group or prodrugs. $R_5$ is more preferably a hydrogen atom, an OH group or a prodrug of ibuprofen.

According to an embodiment, Z is a cationic polar functional group selected from quaternary ammonium groups, tertiary ammonium, secondary ammonium such as ammonium groups may be included in an aliphatic chain, a 5-membered ring, a 5-membered heterocycle comprising 1, 2 or 3 nitrogen atoms, a 5-membered heteroaryl comprising 1, 2, 3 or 4 nitrogen atoms, a 6-membered ring, a 6-membered heterocycle comprising 1, 2, 3 or 4 nitrogen atoms, a 6-membered heteroaryl comprising 1 or 2 nitrogen atoms, phosphonium, such as the phosphonium groups can be included in an aliphatic chain, a 5-membered ring, a 6-membered ring, arsonium, such as the arsonium groups can be included in an aliphatic chain and a combination thereof. According to a preferred embodiment, Z is a cationic polar functional group selected from quaternary ammonium groups, such as the ammonium groups can be included in an aliphatic chain, a 6-membered heteroaryl comprising 1 or 2 nitrogen atoms, phosphonium, such as the phosphonium groups can be included in an aliphatic chain, and arsonium, such as the arsonium groups can be included in an aliphatic chain and a combination thereof. In these embodiments, Z is more preferably a quaternary ammonium, phosphonium and arsonium group more preferably, Z is a quaternary ammonium and even more preferably Z is a —N$^+$Me$_3$ function.

According to another embodiment, Z is a zwitterionic polar functional group selected from the aminocarboxylate, aminosulfonate, carboxybetaine groups such as the ammonium group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms, a sulfobetaine function such as the ammonium group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms, a betaine function such as the ammonium group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms, a phosphobetaine function such as the ammonium group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms, a phosphorylcholine, a phosphocholine function and a combination thereof. According to a preferred embodiment, Z is a zwitterionic polar functional group selected from a sulfobetaine function such as the ammonium group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms, and a phosphobetaine function such as the ammonium group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms. In these embodiments, Z is more preferably a sulfobetaine function such as the ammonium group is included in an aliphatic chain, more preferably, Z is a —N$^+$Me$_2$-(CH$_2$)$_3$—SO$_3^-$ function.

According to another embodiment, Z is a neutral polar functional group selected from the amino, alkylamino, dialkylamino groups, such as the dialkylamino group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms, polyethylene glycol (PEG) and a combination thereof. According to a preferred embodiment, Z is a neutral polar functional group selected from the dialkylamino groups, such as the dialkylamino group can be included in an aliphatic chain, a 5-membered ring, a 5-membered heterocycle comprising 1, 2 or 3 nitrogen atoms, a 6-membered ring, a 6-membered heterocycle comprising 1, 2, 3 or 4 nitrogen atoms and polyethylene glycol (PEG). In these embodiments, Z is more preferably adialkylamino group included in an aliphatic chain or a polyethylene glycol, preferably, Z is a —NMe$_2$ group.

According to another embodiment, Z is an anionic polar functional group selected from the carboxylate, sulphonate, sulphate, or phosphate groups and a combination thereof. According to a preferred embodiment, Z is an anionic polar functional group selected from the carboxylate, sulphate, or phosphate groups.

According to an embodiment, the compound of the invention is cationic. According to another embodiment, the compound is neutral. According to another embodiment, the compound is zwitterionic. According to another embodiment, the compound is anionic.

According to an embodiment, a is equal to 1. According to an embodiment, a is equal to 0.

According to an embodiment, n is equal to n', m equal to m', p equal to p' and q equal to q'.

According to an embodiment, the sum of m and p is equal to 2. According to another embodiment, the sum of m and p is equal to 1. According to an embodiment, the sum of m' and p' is equal to 2. According to another embodiment, the sum of m' and p' is equal to 1.

According to an embodiment, n, n', q and q' are each independently an integer from 4 to 10, preferably from 6 to 9. According to a specific embodiment, n and n' are equal to 7 and q and q' are equal to 8.

According to a preferred embodiment, the compound of the invention is a compound of formula (IIa):

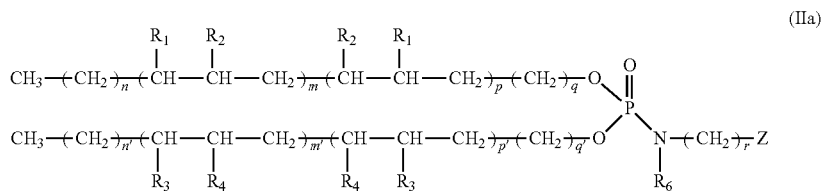

(IIa)

wherein R$_1$, R$_2$, R$_3$, R$_4$, Z, n, n', m, m', p, p', q and q' are such as defined hereinabove, R$_6$ is a hydrogen or an alkyl and r is an integer from 1 to 10.

According to an embodiment, r is an integer from 1 to 7, preferably an integer from 1 to 4.

According to another preferred embodiment, the compound of the invention is a compound of formula (IIb):

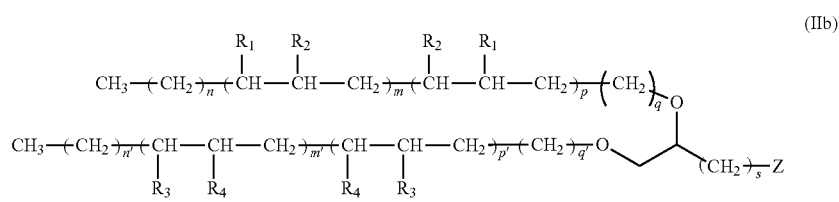

(IIb)

wherein R$_1$, R$_2$, R$_3$, R$_4$, Z, n, n', m, m', p, p', q and q' are such as defined hereinabove and s is an integer from 1 to 10.

According to an embodiment, s is an integer from 1 to 7, preferably an integer from 1 to 4.

According to an embodiment, the compound of the invention is selected from the group comprising the compounds of the table hereinbelow for which X$^-$ is a counterion:

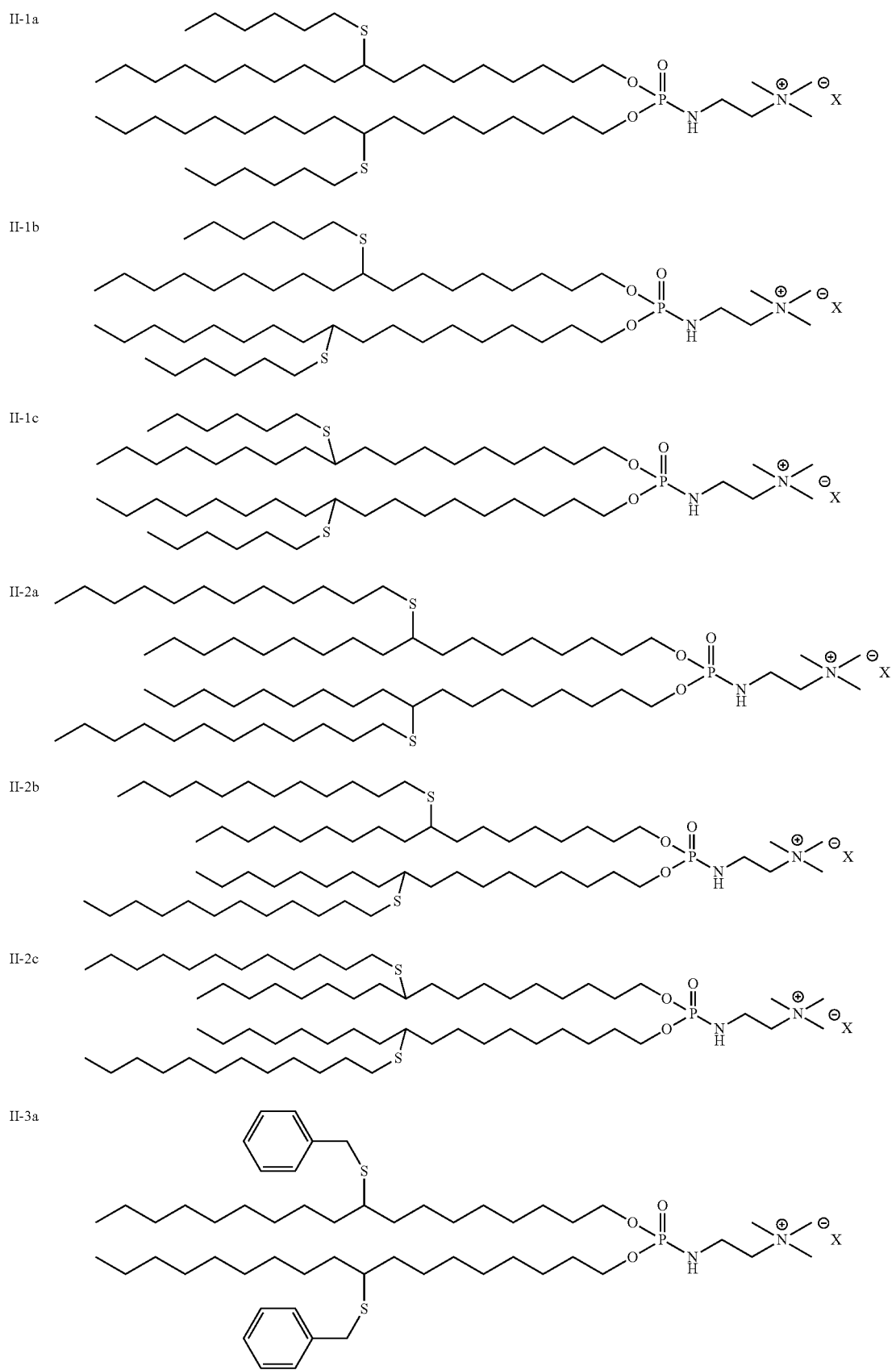

-continued
II-3b
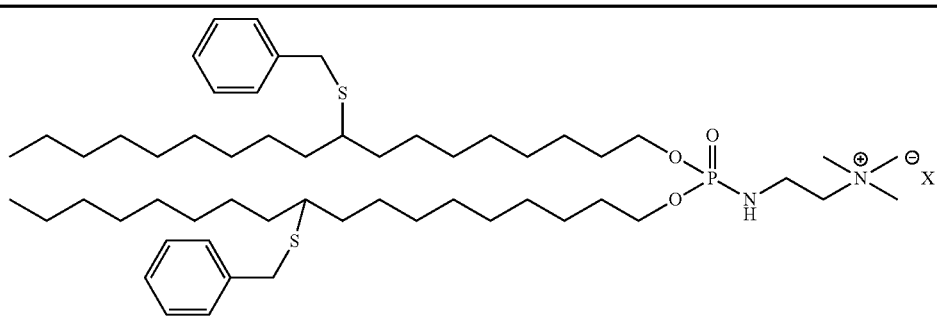
II-3c
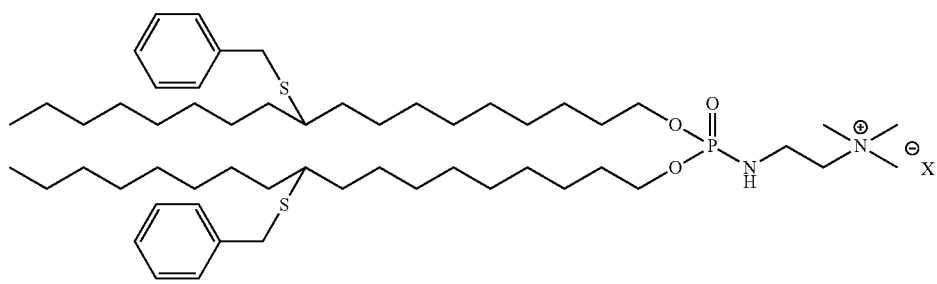
II-4a
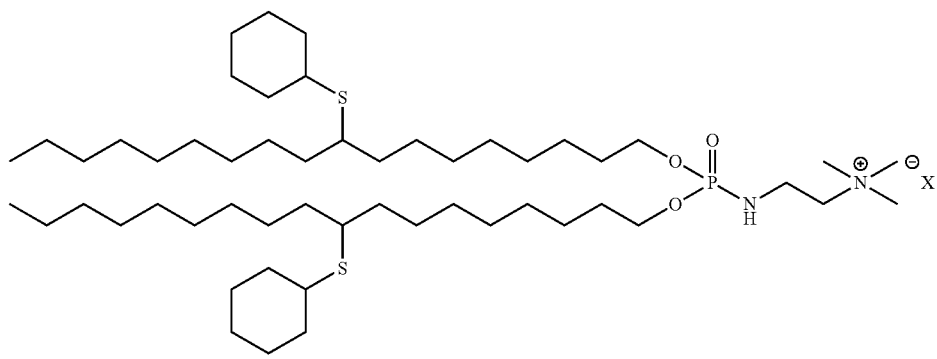
II-4b
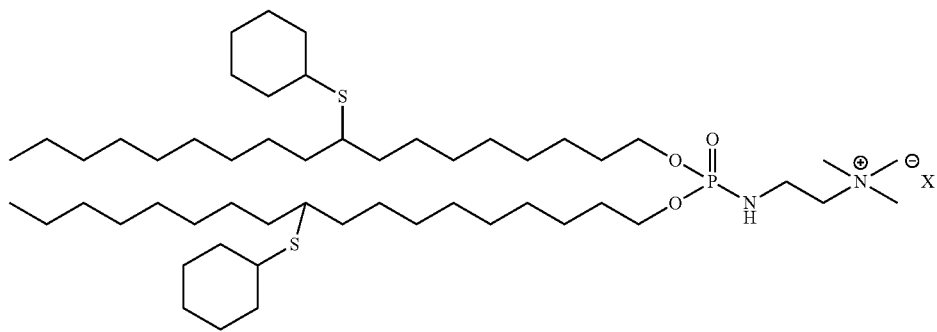
II-4c
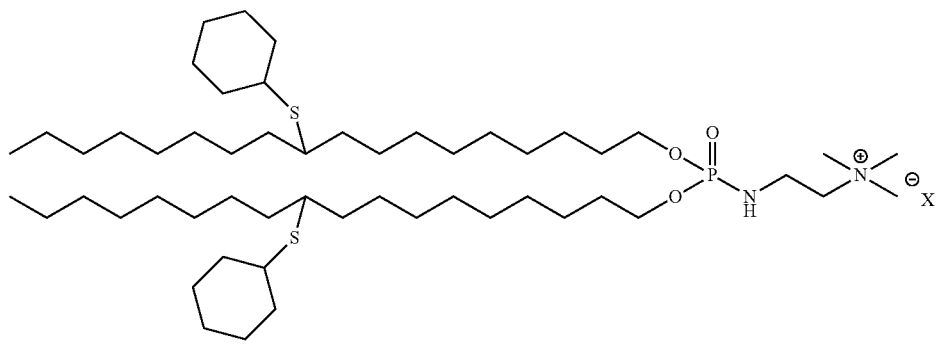

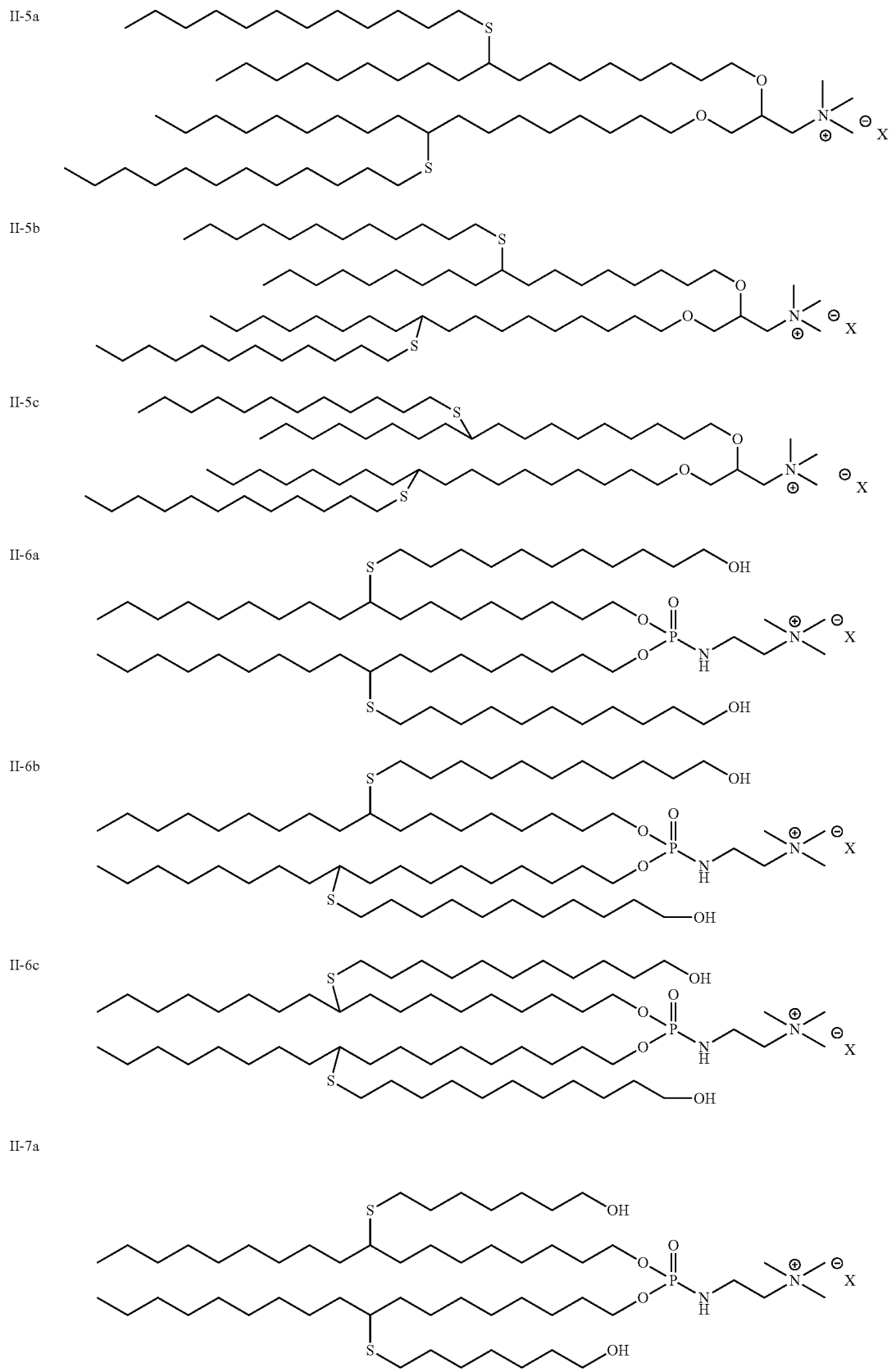

-continued
II-7b
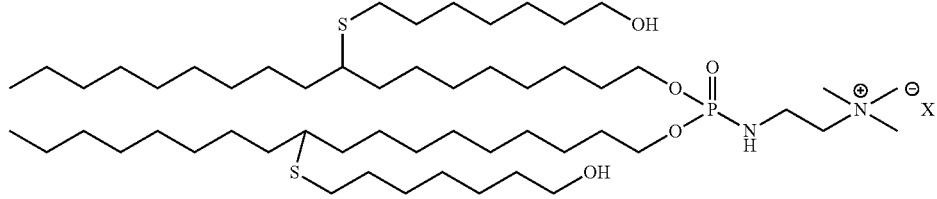
II-7c
II-8a
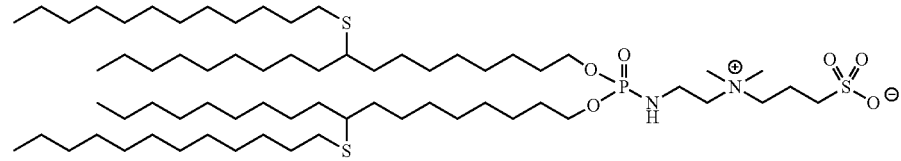
II-8b
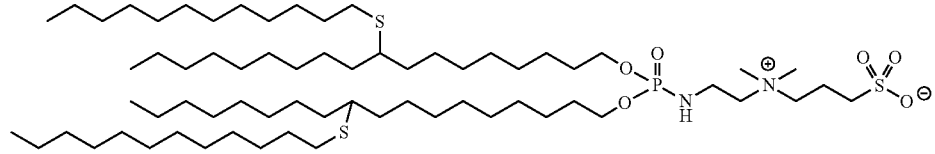
II-8c
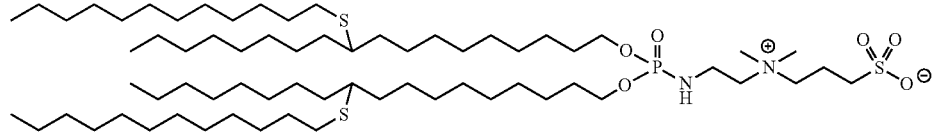
II-9a
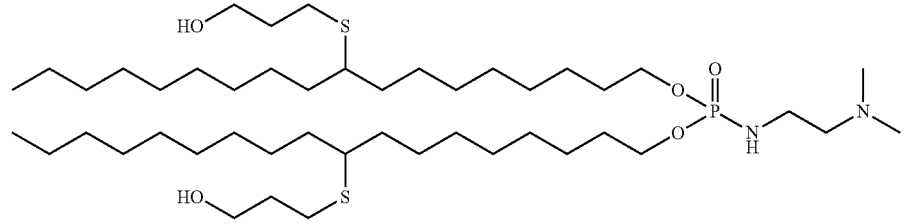
II-9b
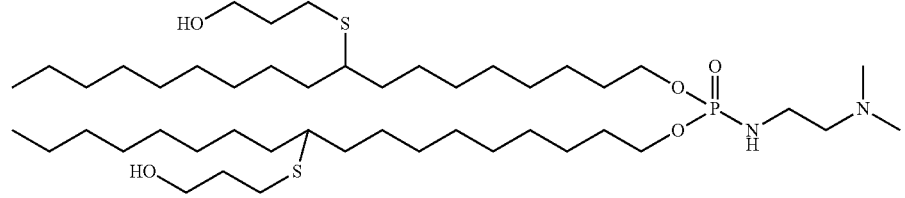
II-9c
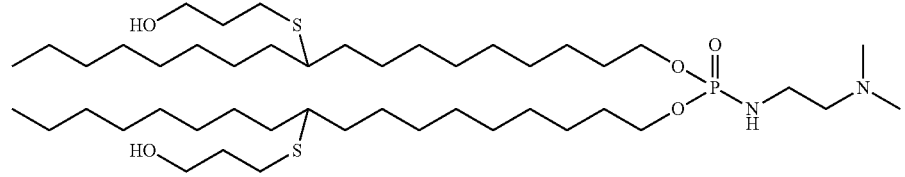

II-10a

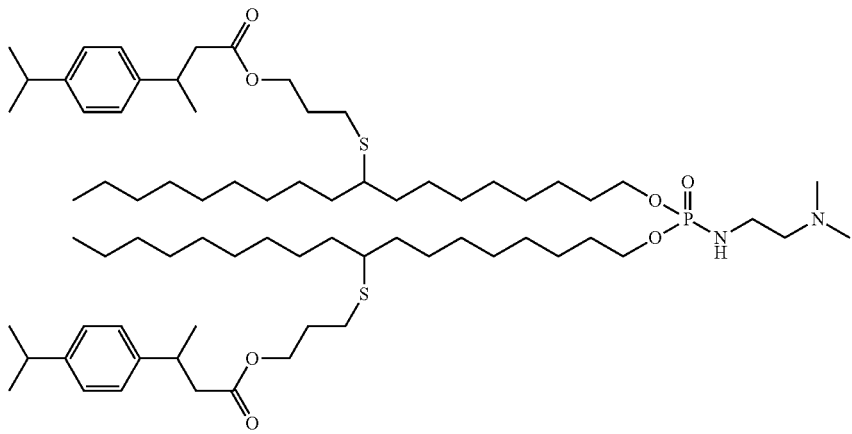

II-10b

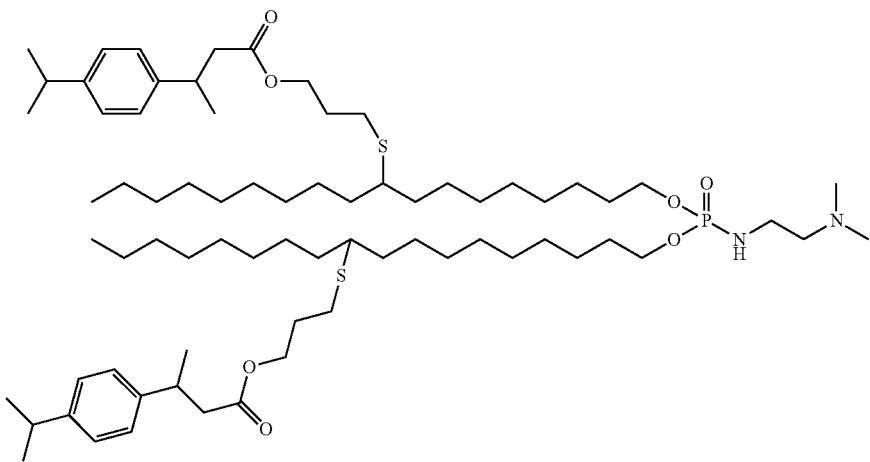

II-10c

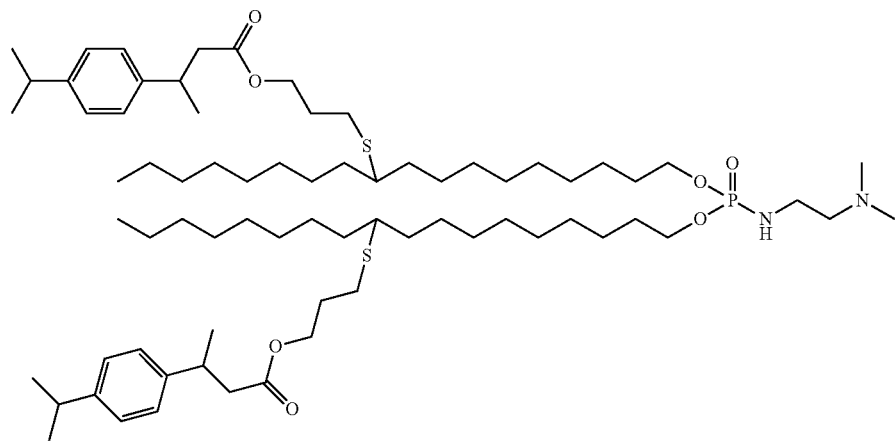

In an embodiment, the counterion is an anion selected from the chloride, bromide, iodide, tosylates, triflates, methylsulphate anions, preferably the counterion is an anion selected from the chloride, bromide, iodide anions.

According to an embodiment, the compound II-1 is a mixture of compounds II-1a, II-1b and II-1c. In the same way, the compound II-X is a mixture of compounds II-Xa, II-Xb and II-Xc.

This invention also relates to a liposome comprising at least one compound of the invention such as described hereinabove. In particular, the invention relates to a liposome that has a hexagonal phase and comprising at least one of the compounds of formula (II), (IIa) or (IIb). According to a preferred embodiment, the liposome has a hexagonal phase and comprises at least one compound of formula (IIa). According to another preferred embodiment, the liposome has a hexagonal phase and comprises at least one compound of formula (IIb).

According to an embodiment, the liposome comprises only compounds that are cationic, i.e. with Z being a cationic polar functional group, of formula (II), (IIa) or (IIb).

According to a preferred embodiment, the liposome comprises only cationic compounds of formula (IIa). According to another preferred embodiment, the liposome comprises only cationic compounds of formula (IIb).

According to an embodiment, the liposome is formed from at least one neutral compound of formula (II), (IIa) or (IIb) in association with at least one unbranched cationic amphiphilic lipid. According to a preferred embodiment, the liposome is formed from at least one neutral compound of formula (IIa) in association with at least one unbranched cationic amphiphilic lipid. According to an embodiment, the unbranched cationic lipid can be N-[1-(2,3-dioleyloxy)propylJ-N,N,N-trimethylammonium chloride (DOTMA) or the compound I-1 of the invention.

According to an embodiment, the liposome has a hexagonal phase. According to an embodiment, the liposome has a direct hexagonal phase. According to an embodiment, the liposome has a reversed hexagonal phase.

The liposomes of the invention can be obtained according to methods known by the skilled artisan.

According to an embodiment, the liposomes can be prepared by evaporation of the organic solvent wherein the amphiphilic lipids of the invention are dissolved, then by putting them in suspension in an aqueous solvent. This operation must take place at a temperature greater than that of the phase transition of the lipids of the invention.

This invention also relates to a lipoplex comprising at least one compound of the invention such as described hereinabove. In particular, the invention relates to a lipoplex that has a hexagonal phase and comprising at least one of the compounds of formula (II), (IIa) or (IIb). According to an embodiment, the lipoplex comprises only compounds which are cationic, i.e. with Z being a cationic polar functional group, of formula (II), (IIa) or (IIb). According to a preferred embodiment, the lipoplex comprises only cationic compounds of formula (IIa). According to another preferred embodiment, the lipoplex comprises only cationic compounds of formula (IIb).

According to an embodiment, the lipoplex is formed from at least one neutral compound of formula (II), (IIa) or (IIb) in association with at least one unbranched cationic amphiphilic lipid of formula (I). According to a preferred embodiment, the lipoplex comprises at least one neutral compound of formula (IIa) as well as at least one unbranched cationic amphiphilic lipid of formula (I). According to an embodiment, the unbranched cationic lipid can be DOTMA or the compound I-1.

According to an embodiment, the lipoplex has a hexagonal phase. According to an embodiment, the lipoplex has a direct hexagonal phase. According to an embodiment, the lipoplex has a reversed hexagonal phase.

The lipoplexes of the invention can be obtained according to methods known by the skilled artisan. The lipoplexes are prepared by mixing a given quantity of DNA with the amphiphilic lipids of the invention. According to an embodiment the charge ratios of the lipoplexes can be between 0.3 and 15.0, preferably between 0.5 and 8.0.

Method

The compounds of the invention can be obtained according to reactions known by the skilled artisan.

This invention also relates to a method for manufacturing the compounds of the invention. In particular, the invention relates to a method of chemical synthesis that makes it possible to easily and quickly modulate the structure of the pre-existing amphiphilic lipids on their lipid portion by means of a reaction of the thiol-ene type.

This invention also relates to the method for producing a compound of formula (II),

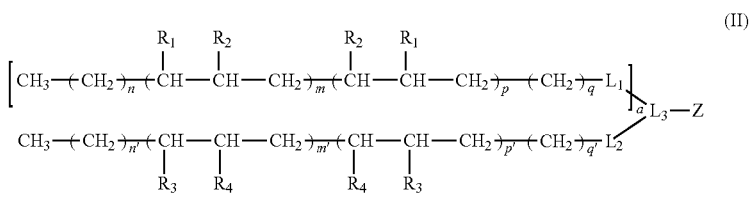

wherein $L_1$ and $L_2$ are each independently a linker, preferably the linker is chosen from a single bond and the alkyl, aryl, alkylaryl, arylalkyl, alkyloxy, alkyloxycarbonyl groups;

$L_3$ is a linker, preferably the linker is chosen from the alkyl, alkylphosphoramidates, alkylthiophosphoramidates, alkylphosphate, alkylthiophosphate, alkylphosphonite, alkylphosphonate, alkylthiophosphonate, alkylphosphoramide, alkylthiophosphoramide, alkyloxy or amine groups;

Z is a polar functional group, said group being cationic, anionic, zwitterionic or neutral;

a is 0 or 1;

n, n', q and q' are each independently an integer from 1 to 15;

m, m', p and p' are each independently an integer from 0 to 4 with the condition that:
at least one of m and p is different from 0;
at least one of m' and p' is different from 0;

$R_1$ and $R_2$ are one a hydrogen and the other a thioether group of formula —S-$L_4$-$R_5$ and $R_3$ and $R_4$ are one a hydrogen and the other a thioether group of formula —S-$L_4$-$R_5$ wherein:

$L_4$ is a linker, preferably the linker is chosen from a single bond and the aminocarbonyl, acylamino, alkylaminocarbonyl, aminothiocarbonyl, alkyloxycarbonyl, alkyl, aryl, cycloalkyl, alkylaryl, arylalkyl, alkyloxy, polyethylene glycol (PEG), polypropylene glycol (PPG) groups, a peptide or a combination thereof; optionally interrupted or terminated by —O—, —S—, —$SO_2$— or a combination thereof, optionally further comprising a residue of a reactive group through which $L_4$ is connected to $R_5$;

$R_5$ is a hydrogen atom, or:
polar group chosen from the group of organic salts of the ammonium, phosphonium, and imidazolium type and protonable neutral heterocycles;
a reactive group chosen from the group comprising the N3, amino, alkylamino, COOH, amide, maleimide, alkyne, SH, OH, ester, activated ester, activated carboxylic acid, halo, nitro, nitrile, isonitrile, acrylamide, aldehyde, ketone, acetals, ketals, anhydride, thiocyanate, isothiocyanate, isocyanate, hydrazine, hydrazides, hydrazones, ethers, oxides, cyanates, diazo, diazonium, sulphides, disulphides, sulphoxides, sulphones, sulphonic acids, sulphinic acids, sulphates, sulphenic acids, amidines, imides, imines, imidates, nitrones, hydroxylamines, oximes, hydroxamic acids thiohydroxamic acids, allenes, ortho esters, sulphites, enamines, ynamines, ureas, pseudo-ureas, semicarbazides, carbodiimides, carbamates group; or a bioactive group chosen from prodrugs, amino acids, peptides, proteins, antibodies, enzymes, polysaccharides, nucleosides, nucleotides, oligonucleotides, fluorophores, chromophores, radioisotopes, the carboranes, and combinations thereof, comprising the following steps:

i) reacting a compound of formula (I)

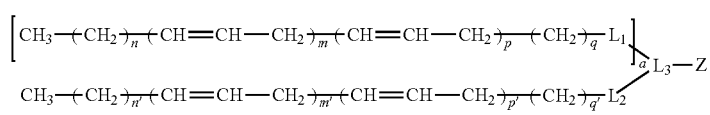

(I)

wherein $L_1$, $L_2$, $L_3$, Z, a, n, n', m, m', p, p', q and q' are such as defined hereinabove;

with a thiol $R_5$-$L_4$-SH wherein $L_4$ and $R_5$ such as defined hereinabove, in the presence of at least one radical initiator;

ii) optionally, reacting the product of the reaction (i) with a bioactive molecule, chosen from prodrugs, amino acids, peptides, proteins, antibodies, enzymes, polysaccharides, nucleosides, nucleotides, oligonucleotides, fluorophores, chromophores, radioisotopes, and carboranes, and combinations thereof.

The preferred embodiments of $L_1$, $L_2$, $L_3$, $L_4$, Z, a, n, n', m, m', p, p', q and q', $R_1$, $R_2$, $R_3$ and $R_4$ defined for the compound (II) hereinabove also apply to the method and to the reagents, i.e. the compound (I) and the compound $R_5$-$L_4$-SH.

According to an embodiment, the step (i) is generally carried out in the presence of an excess of thiol. According to an embodiment, the step (i) is carried out in the presence of a quantity of thiol between 1.1 equivalents and 50 equivalents, preferably between 1.1 and 5 equivalents, more preferably between 1.1 and 4 equivalents. According to an embodiment, when the compound of formula (I) comprises an unsaturation, the step (i) is carried out in the presence of a quantity of thiol greater than or equal to 1.1 equivalent. According to an embodiment, when the compound of formula (I) comprises two unsaturations, the step (i) is carried out in the presence of a quantity of thiol greater than or equal to 2.1 equivalents. According to an embodiment, when the compound of formula (I) comprises x unsaturations, the step (i) is carried out in the presence of a quantity of thiol greater than or equal to (x+0.1) equivalents.

According to an embodiment, the step (i) is generally carried out in the presence of at least one radical initiator. According to an embodiment, the radical initiator can be heat-activated or photoactivated, wherein more preferably, the heat-activated radical initiator is chosen from the group comprising diazo compounds such as azobisisobutyronitrile (AIBN), 2,2'-azobis[2-(2-imidazoline-2-yl)propane]dihydrochloride, azobis (2-amidinopropane)dihydrochloride (ABAH), or azobis-cyanopentanoic acid and the photoactivated radical initiator is chosen from the group comprising camphorquinone, benzophenone, benzophenone derivatives, acetophenone, acetophenone derivatives, such as α-hydroxycycloalkyl phenyl ketones or 2-hydroxy-2-methyl-1-phenylpropanone, dialcoxyacetophenones, such as 2,2-dimethoxy-2-phenylacetophenone, α-hydroxy- or α-amino-acetophenones, such as (4-methylthiobenzoyl)-1-methyl-1-morpholinoethane, preferably acetophenone and acetophenone derivatives, more preferably 2,2-dimethoxy-2-phenylacetophenone.

According to an embodiment, the step (i) is generally carried out in the presence of at least one heat-activated radical initiator. According to another embodiment, the step (i) is generally carried out in the presence of at least one photoactivated radical initiator. According to a preferred embodiment, the step (i) is carried out in the presence of 2,2-dimethoxy-2-phenylacetophenone. According to a preferred embodiment, the step (i) is carried out in the presence of a photoactivated radical initiator. According to a preferred embodiment, the step (i) is carried out only in the presence of 2,2-dimethoxy-2-phenylacetophenone.

According to an embodiment, the step (i) is carried out in the presence of a radical initiator at a content of 0.1% to 50% by mol in relation to unbranched amphiphilic lipid of formula (I), preferably, at a content of 0.1% to 25% by mol in relation to unbranched amphiphilic lipid of formula (I) and even more preferably at a content of 0.5% to 15% by mol in relation to unbranched amphiphilic lipid of formula (I).

According to an embodiment, the step (i) is carried out in the absence of solvent. According to an embodiment, the step (i) is carried out at ambient temperature. According to an embodiment, the step (i) is carried out under UV radiation. According to an embodiment, the step (i) is carried out under an inert atmosphere. According to an embodiment, the compound obtained is purified using chromatographic techniques known by the skilled artisan.

Uses

The invention relates to a composition comprising a compound of Formula II, a liposome and/or a lipoplex according to the invention and a physiologically acceptable vehicle. According to an embodiment, the composition of the invention is a pharmaceutical composition comprising a compound of Formula II in combination with a pharmaceutically acceptable vehicle. According to an embodiment the compound of formula II is a compound of formula IIa. According to another embodiment the compound of formula II is a compound of formula IIb.

The invention relates to a medicament comprising a compound of Formula II, a liposome and/or a lipoplex according to the invention. The invention relates to a medicament comprising a compound of Formula II. According to an embodiment the compound of formula II is a compound of formula IIa. According to another embodiment the compound of formula II is a compound of formula IIb.

The uses described hereinbelow relate to the use of a compound of Formula II, of a pharmaceutical composition or of a medicament according to this invention.

This invention also relates to the use of a compound of Formula II of the invention or of a liposome of the invention or of a lipoplex of the invention for applications in which improved fusion properties are desired.

This invention also relates to a liposome or lipoplex according to the invention for the use thereof for vectorisation in vitro or in vivo, i.e. the transmembrane transfer of a molecule of interest. This invention therefore also relates to the use of the liposome or, of the lipoplex according to the invention for vectorisation in vitro or in vivo, i.e. the transmembrane transfer of a molecule of interest.

According to an embodiment the invention relates to a compound of Formula II of the invention or of the lipoplex obtained by formulation of a compound of the invention for the use thereof in transfection in vivo, for the delivery of prodrugs, sensitisers or imaging agent, for gene therapy, topical treatments or bactericidal activities.

According to an embodiment this invention relates to a compound of Formula II of the invention for the use thereof for the transfection of cells in vivo. According to an embodiment this invention relates to a lipoplex obtained by formulation of a compound of formula II of the invention for the use thereof for the transfection of cells in vivo.

According to an embodiment the invention relates to the use of a compound of Formula II of the invention or of the lipoplex obtained by formulation of a compound of the invention for the transfection of cells in vitro.

According to an embodiment, this invention relates to a compound of Formula II of the invention for the use thereof for the delivery of prodrugs, sensitisers or imaging agent. According to an embodiment, this invention relates to a liposome or lipoplex according to the invention for the use thereof for the delivery of prodrugs, sensitisers or imaging agent. According to an embodiment, the invention relates to the use of a compound of the invention or of the lipoplex obtained by formulation of a compound of the invention for the delivery of prodrugs, sensitisers or imaging agent.

According to an embodiment the invention relates to a compound of Formula II of the invention for the therapeutic use thereof in transfection, for the delivery of prodrugs, sensitisers or imaging agent, for gene therapy, topical treatments or bactericidal activities. According to an embodiment the invention relates to a liposome of the invention for the therapeutic use thereof in transfection, for the delivery of prodrugs, sensitisers or imaging agent, for gene therapy, topical treatments or bactericidal activities. According to an embodiment the invention relates to a lipoplex of the invention for the therapeutic use thereof in transfection, for the delivery of prodrugs, sensitisers or imaging agent, for gene therapy, topical treatments or bactericidal activities. According to an embodiment, the invention relates to the use of a compound of the invention, of a liposome or of a lipoplex obtained by formulation of a compound of the invention for gene therapy, topical treatments (dermatology, ophtalmology) or cosmetics or bactericidal activities. According to an embodiment, the invention relates to the therapeutic use of a compound of the invention, of a liposome or of a lipoplex obtained by formulation of a compound of the invention for gene therapy, topical treatments or bactericidal activities.

According to an embodiment, the invention relates to the use of a compound of the invention, of a liposome or of a lipoplex obtained by formulation of a compound of the invention for cosmetic treatments.

According to an embodiment the compound of formula II is a compound of formula IIa. According to another embodiment the compound of formula II is a compound of formula IIb.

When in the formula II, $R_5$ is a prodrug, the invention relates to the use of compounds of formula II, for the treatment and/or the prevention of the disease targeted by the corresponding drug. When in the formula II, $R_5$ is a prodrug, the invention also relates to a method of treating and/or preventing a disease targeted by the corresponding drug comprising the administration to a subject of a compound of Formula II, or a liposome, or a lipoplex according to the invention in a quantity that is effective in improving and/or preventing said disease. When in the formula II, $R_5$ is a prodrug, the invention also relates to the use of compounds of Formula II for the preparation of a medicament for the treatment and/or the prevention of a disease targeted by the corresponding drug.

According to an embodiment, the subject is an animal, more preferably a mammal, more preferably a human.

According to an embodiment, the compounds of formula II, the liposomes and lipoplexes of the invention are formulated in a form that is suitable for injection. The injection may be intradermal, intramuscular, intraperitoneal, or subcutaneous. In an embodiment, the compounds of formula II, the liposomes and lipoplexes are formulated in the form of a solution, such as for example a sterile aqueous solution, a dispersion, an emulsion, a suspension. In order to prevent any contamination by microorganisms, one or several preservatives can be added to the pharmaceutical composition such as antibacterial and antifungal agents such as parabens, chlorobutanol, phenol, sorbic acid, thiomersal and other similar agents. It may also be preferable to add to the pharmaceutical composition one or more isotonic agents such as sugars or sodium chloride in order to reduce the pain caused by the injection.

EXAMPLES

Figure 1:
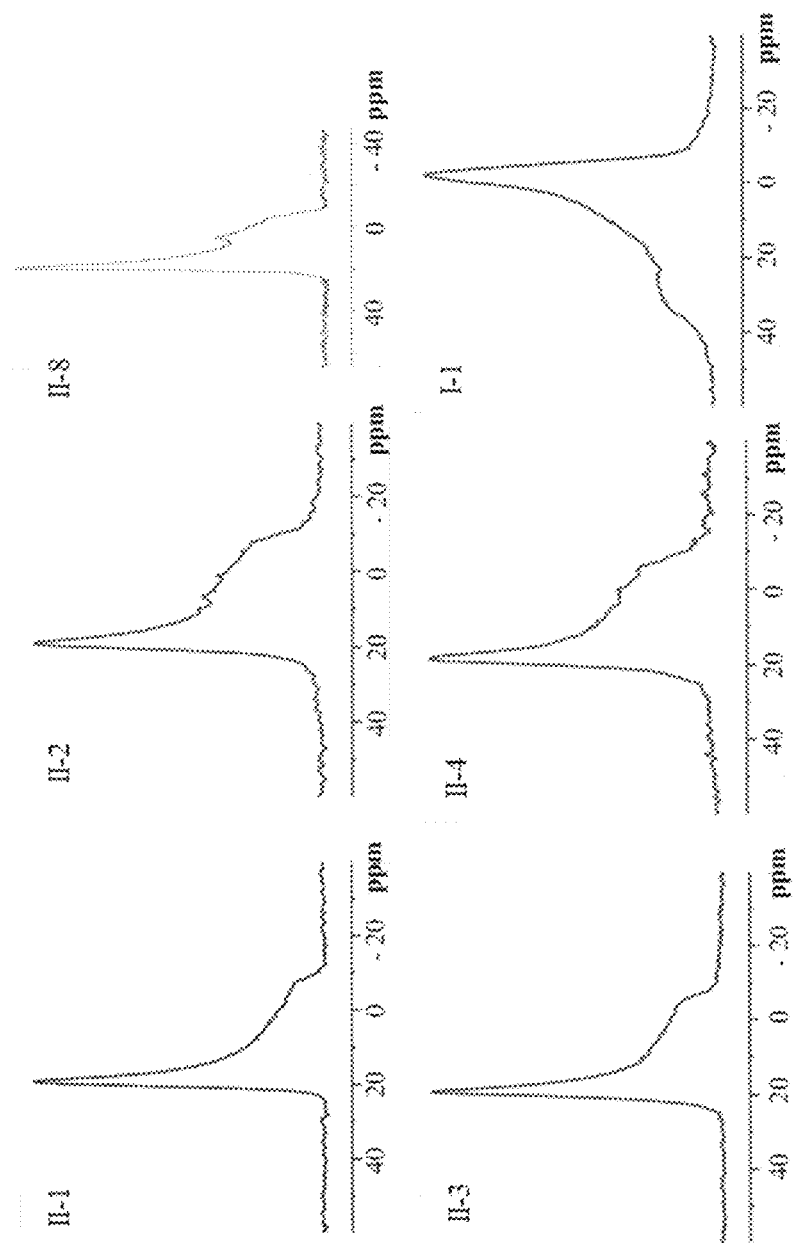
FIG. 1 is a set of NMR $^{31}$P spectra (Hahn echo) of the compounds I-1, II-1, II-2, II-3, II-4 and II-8 (in a mixture with the compound I-1 with a ratio 1/1) carried out at ambient temperature.

This invention will be understood better when reading the following examples which show the invention in a non-limiting way.

SYNTHESIS

Abbreviations

DNA: deoxyribonucleic acid;
RNA: ribonucleic acid;
siRNA: small interfering RNA;
mRNA: messenger RNA;
° C.: degrees Celsius;
DOTMA: N-[1-(2,3-dioleyloxy)propyl]-N,N,N-trimethyl-ammonium chloride;
DCC: N,N'-dicyclohexylcarbodiimide;
DMEM: Dulbecco's modified Eagle's essential minimum medium;
eq.: equivalent;
EGFP-Luc: Enhanced green fluorescent protein-luciferase;
μs: microsecond;
Ppm: parts per million;
CR: charge ratio;
NMR: nuclear magnetic resonance;
TMS: tetramethylsilane;
UV: ultra-violet.

Materials

The solvents used were purified according to the usual methods.

The starting substrates were supplied by Aldrich, TCI or Alfa Aesar and used without any additional purification. The 2-((bis(E)-octadec-9-en-1-yloxy)phosphoryl)amino)-N,N,N-trimethylthanaminium iodide (reagent I-1) was synthesised according to the literature. (Le Corre, S. S.; Berchel, M.; Belmadi, N.; Denis, C.; Haelters, J. P.; Le Gall, T.; Lehn, P.; Montier, T.; Jaffrès, P. A. Org. Biomol. Chem., 2014, 12, 1463-1474.).

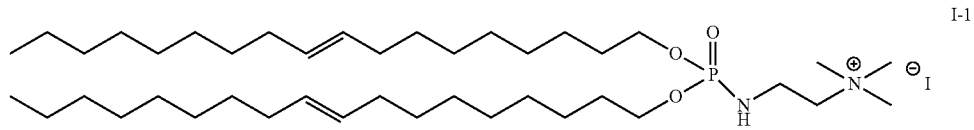

I-1

All of the compounds were characterised by nuclear magnetic resonance spectroscopy (NMR) $^1$H (500.13 or 400.133 or 300.135 MHz), $^{13}$C (125.773 or 75.480 MHz) and $^{31}$P (161.970 or 121.498 MHz) (Bruker AC 300, Avance DRX 400 and Avance DRX 500 Spectrometers). The J coupling constants are given in Hertz. The following abbreviations are used: s for singlet, d for doublet, t for triplet, q for quadruplet, qt for quintuplet, m for multiplet, dd for doublet of doublets and dt for doublet of triplets.

The compounds were also characterised by mass spectrometry (Bruker Autoflex MALDI TOF-TOF III LRF200 CID).

Results

1) Synthesis of Zwitterionic Reagents

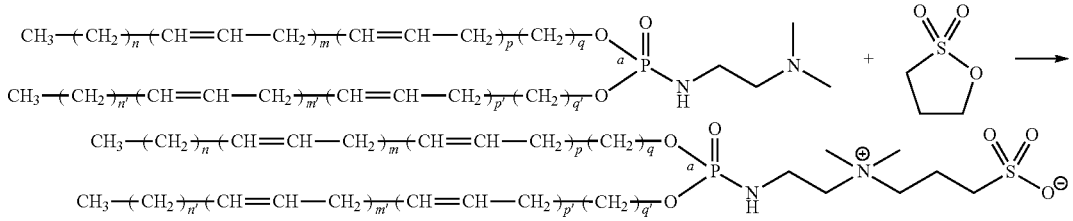

To a solution of dioleyl phosphoramide (1 eq) in the chloroform, is added propanesulfone (1.2 eq). The reaction medium is stirred for 72 h at ambient temperature. The raw product obtained is then purified by flash chromatography on a silica gel column.

The following compound was synthesised according to the method described hereinabove.

Compound I-2: Yield: 44%, $^{31}$P NMR: δ (ppm, reference 85% $H_3PO_4$: 0 ppm in $CDCl_3$): 9.4; $^1$H NMR: δ (ppm, reference TMS: 0 ppm in $CDCl_3$): 0.85 to 0.89 (t, $^3J_{H-H}$=6.8 Hz, 6H, $CH_3$—$CH_3$), 1.21 to 1.29 (m, 46H, $CH_2$ fatty chain), 1.62 to 1.65 (m, 4H, $CH_2$—$CH_2$—O—P), 1.96 to 2.01 (m, 8H, $CH_2$—CH=CH—$CH_2$), 2.19 to 2.26 (m, 2H, $^+$N—$CH_2$—$CH_2$—$CH_2$—S), 2.89 to 2.91 (m, 2H, $^+$N—$CH_2$—$CH_2$—$CH_2$—S), 3.24 (s, 6H, $(CH_3)_2N^+$), 3.41 to 3.47 (m, 2H, $^+$N—$CH_2$—$CH_2$), 3.51 to 3.61 (m, 2H, N—$CH_2$—$CH_2$-$^+$N—$CH_2$), 3.67 to 3.72 (m, 2H, N—$CH_2$—$CH_2$—$^+$N—$CH_2$), 3.90 to 3.96 (m, 4H, $CH_2$—O—P), 4.82 to 5.00 (m, 1H, P—NH), 5.29 to 5.37 (m, 4H, CH=CH); $^{13}$C NMR: δ (ppm, reference TMS: 0 ppm in CDCl$_3$): 14.2 ($CH_3$—$CH_2$), 25.5 ($CH_2$ fatty chain), 27.2 ($CH_2$ fatty chain), 28.9 to 30.5 ($CH_2$ fatty chain), 31.9 ($CH_2$ fatty chain), 51.3 ($(CH_3)_2N^+$), 67.0 ($CH_2$—O—P), 129.9 to 130.2 (CH=CH).

2) Synthesis of the Compounds of the Invention
2.1) Click Chemistry with Amphiphilic Lips

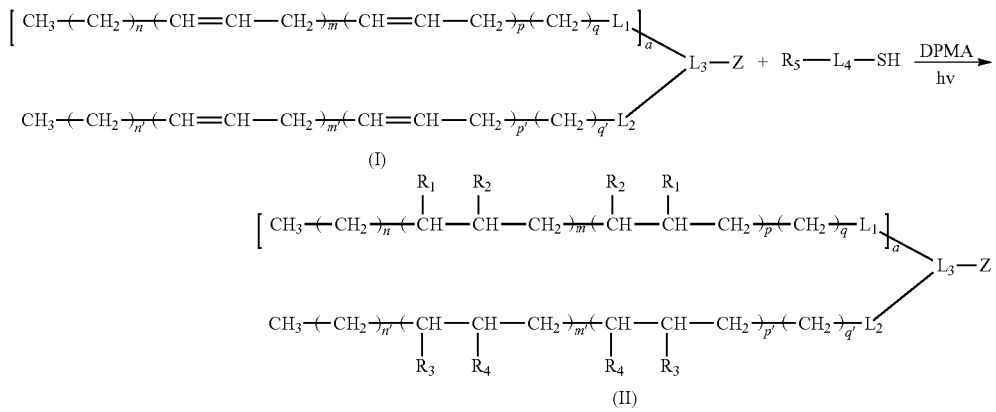

The compound of formula (I) (1 eq) and the thiol (3.5 eq) are mixed in a glass tube, which is placed in an ultrasound bath until complete dissolution of the compound of formula (I) (10 to 20 minutes). The mixture is degassed under argon, before the adding of 2,2-dimethoxy-2-phenylacetophenone (10% by weight). The solution is placed under UV, at ambient temperature, for 4 hours. The raw product obtained is then purified by flash chromatography on a silica gel column.

The following compounds were synthesised according to the method described hereinabove.

Compounds II-1: Yield: 42% (120 mg); $^{31}$P NMR: δ (ppm, reference 85% $H_3PO_4$: 0 ppm in CHCl$_3$)=8.6; $^1$H NMR: δ (ppm, reference TMS: 0 ppm in CHCl$_3$)=0.84 to 0.91 (m, 12H, $CH_3$—$CH_2$), 1.30 to 1.66 (m, 76H, $CH_2$ fatty chain), 2.43 to 2.47 (t, $^3J_{H—H}$=8.0 Hz, 4H, $CH_2$—S), 2.50 to 2.56 (qt, $^3J_{H—H}$=6 Hz, 2H, $(CH_2)_2CH$—S), 3.45 (s, 9H, $^+N(CH_3)_3$), 3.55 to 3.63 (m, 2H, $CH_2$—NH), 3.85 to 3.88 (m, 2H, $CH_2$—$^+N(CH_3)_3$), 3.95 to 3.99 (m, 4H, $CH_2$—O—P), 4.40 to 4.53 (m, 1H, NH); $^{13}$C NMR: δ (ppm, reference TMS: 0 ppm in CHCl$_3$)=13.8 ($CH_3$—$CH_2$), 22.3 to 31.6 ($CH_2$ fatty chain), 34.6 ($CH_2$—CH—$CH_2$), 35.9 ($CH_2$—NH), 45.6 (CH—S), 54.5 ($^+N(CH_3)_3$), 66.4 ($CH_2$—$^+N(CH_3)_3$), 66.8 (d, $^2J_{C—P}$=5.2 Hz, $CH_2$—O—P); MALDI-TOF: $[M]^+_{calculated}$ for $C_{53}H_{112}N_2O_3PS_2$=919.785, $[M]^+_{measured}$=919.775;

Compounds II-2: Yield: 65% (150 mg); NMR $^{31}$P: δ (ppm, reference 85% $H_3PO_4$: 0 ppm in CHCl$_3$)=8.6; NMR $^1$H: δ (ppm, reference TMS: 0 ppm in CHCl$_3$)=0.85 to 0.88 (t, $^3J_{H—H}$=6.4 Hz, 12H, $CH_3$—$CH_2$), 1.24 to 1.66 (m, 76H, fatty chain), 2.43 to 2.47 (t, $^3J_{H—H}$=8.0 Hz, 4H, $CH_2$—S), 2.51 to 2.55 (qt, $^3J_{H—H}$=8.0 Hz, 2H, $(CH_2)_2CH$—S), 3.45 (s, 9H, $^+N(CH_3)_3$), 3.50 to 3.61 (m, 2H, $CH_2$—NH), 3.83 to 3.86 (m, 2H, $CH_2$—$^+N(CH_3)_3$), 3.95 to 4.00 (m, 4H, $CH_2$—O—P), 4.30 to 4.43 (m, 1H, NH); NMR $^{13}$C: δ (ppm, reference TMS: 0 ppm in CHCl$_3$)=13.9 ($CH_3$—$CH_2$), 22.5 ppm to 31.8 ($CH_2$ fatty chain), 34.8 ($CH_2$—CH—$CH_2$), 36.0 ($CH_2$—NH), 45.8 (CH—S), 54.7 ($^+N(CH_3)_3$), 66.6 ($CH_2$—$^+N(CH_3)_3$), 66.9 (d, $^2J_{C—P}$=5.3 Hz, $CH_2$—O—P); MALDI-TOF: $[M]^+_{calculated}$=1087.975; $[M]^+_{measured}$ for $C_{65}H_{136}N_2O_3PS_2$=1087.972;

Compound II-3: Yield: 58% (150 mg); $^{31}$P NMR: δ (ppm, reference 85% $H_3PO_4$: 0 ppm in CHCl$_3$)=8.7; $^1$H NMR: δ (ppm, reference TMS: 0 ppm in CHCl$_3$)=0.83 to 0.91 (m, 6H, $CH_3$—$CH_2$), 1.25 to 1.68 (m, 60H, fatty chain), 2.45 to 2.51 (qt, $J_{H—H}$=6.4 Hz, 2H, $(CH_2)_2CH$—S), 3.43 (s, 9H, $^+N(CH_3)_3$), 3.48 to 3.52 (m, 2H, $CH_2$—NH), 3.68 (s, 4H, $CH_2$-Ph), 3.83 to 3.86 (m, 2H, $CH_2$—$^+N(CH_3)_3$), 3.96 to 4.01 (m, 4H, $CH_2$—O—P), 4.30 to 4.45 (m, 1H, NH), 7.19 to 7.33 (m, 10H, CH aromatic); $^{13}$C NMR: δ (ppm, reference TMS: 0 ppm in CHCl$_3$)=14.1 ($CH_3$—$CH_2$), 22.6 to 31.8 ($CH_2$ fatty chain), 34.5 ($(CH_2)_2$—CH—S), 35.0 ($CH_2$-Ph), 45.3 ($(CH_2)_2$—CH—S), 54.8 ($(CH_3)_3N^+$), 66.6 ($CH_2$—$^+N(CH_3)_3$), 67.1 (d, $^2J_{P—C}$=5.3 ppm, $CH_2$—O—P), 126.7 (CH aromatic), 128.3 to 129.0 (CH aromatic), 138.9 (quaternary C); MALDI-TOF: $[M]^+_{calculated}$ for $C_{55}H_{100}N_2O_3PS_2$=931.691; $[M]^+_{measured}$=931.686;

Compound II-4: Yield: 51% (133 mg); $^{31}$P NMR: δ (ppm, reference 85% $H_3PO_4$: 0 ppm in CHCl$_3$)=8.6; $^1$H NMR: δ (ppm, reference TMS: 0 ppm in CHCl$_3$)=0.81 to 0.87 (t, $^3J_{H—H}$=8 Hz, 6H, $CH_3$—$CH_2$), 1.24 to 1.90 (m, 80H, fatty chain), 2.58 to 2.62 (m, 4H, CH—S—CH), 3.53 (s, 9H, $^+N(CH_3)_3$), 3.50 to 3.60 (m, 2H, $CH_2$—NH), 3.83 to 3.85 (m, 2H, $CH_2$—$^+N(CH_3)_3$), 3.93 to 3.98 (m, 4H, $CH_2$—O—P), 4.30 to 4.40 (m, 1H, NH); $^{13}$C NMR: δ (ppm, reference TMS: 0 ppm in CHCl$_3$)=14.1 ($CH_3$—$CH_2$), 22.6 to 31.9 ($CH_2$ fatty chain), 34.3 ($CH_2$ cyclohexyl), 35.5 ($(CH_2)_2$—CH—S), 36.2 ($CH_2$—NH), 42.6 (CH cyclohexyl), 44.2 ($(CH_2)_2$—CH—S), 54.9 ($^+N(CH_3)_3$), 66.7 ($CH_2$—$^+N(CH_3)_3$), 67.1 (P—O—$CH_2$); MALDI-TOF: $[M]^+_{calculated}$ for $C_{53}H_{108}N_2O_3PS_2$=915.753; $[M]^+_{measured}$=915.741;

Compound II-5: Yield: 61% (199 mg); $^1$H NMR: δ (ppm, reference TMS: 0 ppm in CDCl$_3$)=0.83 to 0.87 (t, $^3J_{H—H}$=6.6 Hz, 12H), 1.23 to 1.24 (m, 73H, $CH_2$ fatty chain), 1.35 to 1.37 (m, 12H, $CH_2$ fatty chain), 1.46 to 1.54 (m, 16H, $CH_2$—$CH_2$—S, $CH_2$—CH—S and $CH_2$ fatty chain), 2.41 to 2.45 (t, $^3J_{H—H}$=7.4 Hz, 4H, $CH_2$—S), 2.48 to 2.55 (qt, $^3J_{H—H}$=7.3 Hz, 2H, $(CH_2)$—CH—S), 3.37 to 3.56 (m, 15H, OCH$_2$ and $^+N(CH_3)_3$), 3.65 to 3.69 (m, 1H, OCH), 3.95 to 3.99 (m, 2H, OCH$_2$); $^{13}$C NMR: δ (ppm, reference TMS: 0 ppm in CDCl$_3$)=14.1 (CH$_3$—CH$_2$), 22.7 (CH$_2$ fatty chain), 26.0 (CH$_2$ fatty chain), 26.2 (CH$_2$ fatty chain), 26.8 (CH$_2$ fatty chain), 29.0 to 29.9 (CH$_2$ fatty chain), 30.35 (CH$_2$—S—CH), 31.90 (CH$_2$ fatty chain), 34.91 (CH$_2$ fatty chain), 46.88 ((CH$_2$)$_2$—CH—S), 54.79 (+N(CH$_3$)$_3$), 67.93 (OCH$_2$), 68.38 (OCH$_2$), 69.31 (OCH$_2$), 72.01 (OCH$_2$), 73.63 (OCH);

Compound II-6: Yield: 48% (140 mg); $^{31}$P NMR: δ (ppm, reference 85% H$_3$PO$_4$: 0 ppm in CDCl$_3$): 8.3; $^1$H NMR: δ (ppm, reference TMS: 0 ppm in CDCl$_3$): 0.85 to 0.89 (t, $^3J_{H—H}$=8 Hz, 6H, CH$_3$—CH$_2$), 1.24 to 1.56 (m, 75H, CH$_2$ fatty chain), 1.49 to 1.56 (m, 12H, CH$_2$ fatty chain), 1.63 to 1.66 (m, 4H, CH$_2$—CH$_2$—O), 1.95 to 2.06 (m, 4H, CH$_2$—CH$_2$—OH), 2.43 to 2.47 (t, $^3J_{H—H}$=7.2 Hz, 4H, CH$_2$—S), 2.51 to 2.54 (m, 2H, CH—S), 3.44 (s, 9H, (CH$_3$)$_3$N$^+$), 3.48 to 3.58 (m, 2H, $^+$N—CH$_2$—CH$_2$), 3.59 to 3.63 (t, $^3J_{H—H}$=6.8 Hz, 4H, CH$_2$—OH), 3.85 to 3.88 (m, 2H, CH$_2$—O—P), 3.96 to 4.01 (m, 4H, CH$_2$—O—P), 4.51 to 4.62 (m, 1H, NH—P); 13C NMR: δ (ppm, reference TMS: 0 ppm in CDCl$_3$): 14.1 (CH$_3$—CH$_2$), 22.6 to 36.0 (CH$_2$ fatty chain), CH$_2$—S), 39.2 (CH$_2$—NH—P), 45.9 ((CH$_2$)$_2$—CH—S), 54.8 (+N(CH$_3$)$_3$), 62.8 (CH$_2$—CH$_2$—OH), 66.5 (CH$_2$—$^+$N(CH$_3$)$_3$), 67.2 to 67.3 (d, $^2J_{H—H}$=22 Hz, CH$_2$—O—P);

Compound II-7: Yield: 23% (65 mg); $^{31}$P NMR: δ (ppm, reference 85% H$_3$PO$_4$: 0 ppm in CDCl$_3$): 8.2; $^1$H NMR: δ (ppm, reference TMS: 0 ppm in CDCl$_3$): 0.86 to 0.89 (t, $^3J_{H—H}$=6.4 Hz, 6H, CH$_3$—CH$_2$), 1.24 to 1.37 (m, 68H, CH$_2$ fatty chain), 1.46 to 1.66 (m, 16H, CH$_2$ fatty chain), 2.29 to 2.40 (m, 4H, CH$_2$—CH$_2$—OH), 2.44 to 2.47 (t, $^3J_{H—H}$=7.2 Hz, 4H, CH$_2$—S), 2.51 to 2.53 (m, 2H, CH—S), 3.45 (s, 9H, (CH$_3$)$_3$N$^+$), 3.47 to 3.54 (m, 2H, $^+$N—CH$_2$—CH$_2$), 3.59 to 3.63 (t, $^3J_{H—H}$=6.8 Hz, 4H, CH$_2$—OH), 3.86 to 3.88 (m, 2H, CH$_2$—NH—P), 3.97 to 4.02 (m, 4H, CH$_2$—O—P), 4.51 to 4.62 (m, 1H, NH—P); $^{13}$C NMR: δ (ppm, reference TMS: 0 ppm in CDCl$_3$): 14.1 (CH$_3$—CH$_2$), 22.7 to 36.1 (CH$_2$ fatty chain and CH$_2$—S and CH$_2$—CH$_2$—OH), 45.9 (CH—S), 54.9 ((CH$_3$)$_3$N$^+$), 62.8 (CH$_2$—OH), 66.5 (CH$_2$—NH—P), 67.4 to 67.5 (d, $^2J_{P—C}$=21 Hz, CH$_2$—O—P);

Compound II-8: Yield: 51%, $^{31}$P NMR: δ (ppm, reference 85% H$_3$PO$_4$: 0 ppm in CDCl$_3$): 9.5, $^1$H NMR: δ (ppm, reference TMS: 0 ppm in CDCl$_3$): 0.86 to 0.88 (t, $^3J_{H—H}$=6.8 Hz, 12H, CH$_3$—CH$_2$), 1.24 to 1.57 (m, 89H, CH$_2$ fatty chain), 1.63 to 1.64 (m, 4H, CH$_2$—CH$_2$—O—P), 2.18 to 2.26 (m, 2H, $^+$N—CH$_2$—CH$_2$—CH$_2$—S), 2.42 to 2.46 (t, $^3J_{H—H}$=7.4 Hz, 4H, CH$_2$—S—CH(CH$_2$)$_2$), 2.49 to 2.54 (st, $^3J_{H—H}$=6.2 Hz, 2H, CH$_2$—S—CH(CH$_2$)$_2$), 2.88 to 2.90 (m, 2H, CH$_2$—S—O), 3.22 (s, 6H, (CH$_3$)$_2$N$^+$), 3.42 to 3.47 (m, 2H, CH$_2$—NH), 3.50 to 3.60 (m, 2H, P—NH—CH$_2$), 3.66 to 3.69 (m, 2H, $^+$N—CH$_2$—CH$_2$—CH$_2$—S), 3.91 to 3.95 (m, 4H, CH$_2$—CH$_2$—O—P), 4.81 to 4.91 (m, 1H, P—NH); $^{13}$C NMR: δ (ppm, reference TMS: 0 ppm in CDCl$_3$): 14.1 (CH$_3$—CH$_2$), 22.7 (CH$_2$ fatty chain), 25.7 (CH$_2$ fatty chain), 26.8 (CH$_2$ fatty chain), 27.0 (CH$_2$ fatty chain), 29.1 to 30.0 (CH$_2$ fatty chain), 30.4 (CH$_2$—S—CH (CH$_2$)$_2$), 31.9 (CH$_2$ fatty chain), 34.9 to 35.1 (CH$_2$ fatty chain), 46.0 (CH$_2$—S—CH(CH$_2$)$_2$), 51.5 ((CH$_3$)$_2$N$^+$), 66.9 (CH$_2$—O—P);

Compound II-9: $^{31}$P NMR: δ (ppm, reference 85% H$_3$PO$_4$: 0 ppm in CDCl$_3$): 10.1, $^1$H NMR: δ (ppm, reference TMS: 0 ppm in CDCl$_3$): 0.85 to 0.88 (t, $^3J_{H—H}$=6 Hz, 6H, CH$_3$—CH$_2$), 1.27 to 1.55 (m, 56H, CH$_2$ fatty chain), 1.62 to 1.37 (m, 4H, CH$_2$—CH$_2$—O—P), 1.79 to 1.85 (m, 4H, CH$_2$—S—CH—(CH$_2$)$_2$), 1.99 to 2.14 (m, 2H, HO—CH$_2$—CH$_2$—CH$_2$—S), 2.21 (s, 6H, (CH$_2$)$_2$—N), 2.36 to 2.39 (t, $^3J_{H—H}$=5.8 Hz, 2H, CH$_2$—S—CH—(CH$_2$)$_2$), 2.55 to 2.61 (m, 6H, HO—CH$_2$—CH$_2$—CH$_2$—S and CH$_2$—CH$_2$—N), 2.92 to 2.98 (m, 2H, P—NH—CH$_2$), 3.20 to 3.31 (m, 1H, P—NH—CH$_2$), 3.71 to 3.76 (m, 4H, HO—CH$_2$—CH$_2$—CH$_2$—S), 3.93 to 3.99 (m, 4H, CH$_2$—O—P).

2.2) Functionalisation by a Bioactive Group

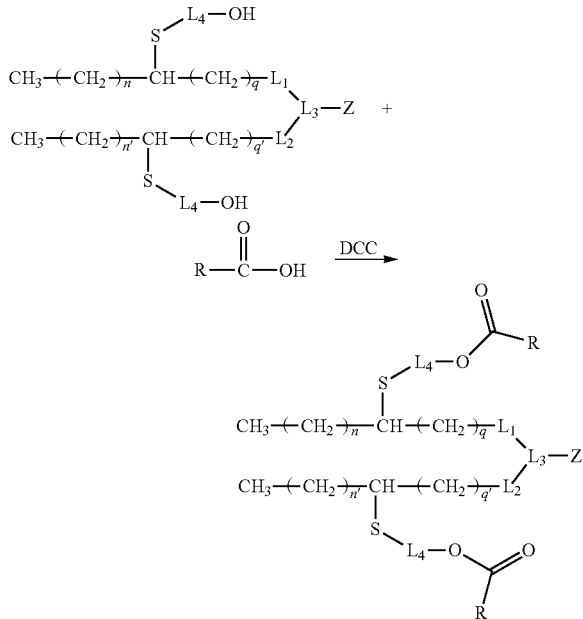

The ester RC(O)OH (2 eq) and the branched compound II (1 eq) are mixed in the anhydrous dichloromethane. After adding DCC (2.2 eq), the reaction medium is stirred for one night. The compound obtained is purified by flash chromatography on a silica gel column.

The following compound was synthesised according to the method C.

Compound II-10: Yield: 15%, $^{31}$P NMR: δ (ppm, reference 85% H$_3$PO$_4$: 0 ppm in CDCl$_3$): 10.1; $^1$H NMR: δ (ppm, reference TMS: 0 ppm in CDCl$_3$): 0.85 to 0.89 (m, 18H, CH$_3$—CH$_2$ and (CH$_3$)$_2$—CH), 1.26 to 1.48 (m, 68H, CH$_2$ fatty chain and CH$_3$—CH-Ph), 1.63 to 1.66 (m, 4H, CH$_2$—CH$_2$—O), 1.79 to 1.84 (m, 4H, S—CH$_2$—CH$_2$—CH$_2$—O), 2.24 (s, 6H, (CH$_3$)$_2$—N), 2.38 to 2.45 (m, 12H, CH$_2$—C (O)—O—CH$_2$, CH$_2$—S and CH—S and CH$_2$—N(CH$_3$)$_2$), 3.89 to 3.02 (m, 4H, CH$_2$—NH—P), 3.34 to 3.42 (m, 1H, NH—P), 3.66 to 3.68 (m, 2H, CH$_3$—CH-Ph), 3.94 to 3.96 (m, 4H, CH$_2$—O—P), 4.12 to 4.15 (t, $^3J_{H—H}$=6.3 Hz, 4H, CH$_2$—O—C(O)—CH$_2$), 7.06 to 7.08 (d, $^3J_{H—H}$=8 Hz, 4H, H$^2$H$^6$/H$^{2'}$ H$^{6'}$), 7.17 to 7.19 (d, $^3J_{H—H}$=8 Hz, 4H, H$^3$H$^5$/H$^{3'}$ H$^{5'}$); $^{13}$C NMR: δ (ppm, reference TMS: 0 ppm in CDCl$_3$): 13.4 (CH$_3$—CH$_2$), 17.5 (CH$_3$—CH-Ph), 22.4 ((CH$_3$)$_2$—CH), 22.65 (CH$_2$ fatty chain), 25.6 (CH$_2$ fatty chain), 26.5 to 26.7 (CH$_2$ fatty chain and CH$_2$—S), 29.0 to 31.9 (CH$_2$ fatty chain), 34.8 (CH$_2$ fatty chain), 38.4 (CH$_2$—NH—P), 44.8 to 46.0 (CH$_2$—N(CH$_3$)$_2$ and CH$_2$—N(CH$_3$)$_2$ and CH—CH$_3$), 59.5 (CH—S), 63.3 (CH$_2$—O—C(O)—CH$_2$), 66.3 (CH$_2$—O—P), 127.1 (C$^3$C$^5$/C$^{3'}$ C$^{5'}$), 129.3 (C$^2$C$^6$/C$^{2'}$ C$^{6'}$), 137.7 (C$^4$/C$^{4'}$), 140.4 (C$^1$/C$^{1'}$), 174.6 (CH$_2$—C(O)—O—CH$_2$).

Studies of the Physical-Chemical Properties of Liposomes and Lipoplexes

1) Structural Organisation—Study Via NMR $^{31}$P

Preparation of the Sample

A stock solution of a cationic lipid is prepared in the chloroform. A volume of stock solution corresponding to a weight in lipids between 50 mg and 100 mg is pipette into a haemolysis tube and the chloroform is evaporated under of flow of $N_2$ in such a way as to obtain a lipid film. 500 μL of water is then added and the mixture is subjected to ultrasound until complete dispersion of the lipid film. The mixture is lysed for one night. A volume of distilled water is then added in order to obtain a solution with a concentration of 100 mg·mL$^{-1}$. In order to ensure the balance of the sample, three cycles −198° C./50° C. are carried out: the sample is placed at −198° C. (liquid nitrogen) for 5 min, then the sample is placed in a water bath at 50° C. for 30 min and is vortexed.

Condition for Acquisition

The NMR $^{31}$P spectra were acquired with a Hahn echo sequence (90°-τ-180°-τ-acq). The acquisition parameters were as follows: spectral window of 200 KHz, a pulse π/2 with a duration of 4.88 is, a recycling period of 5 s and an echo period of 40 μs. The number of acquisitions depends on the volume of the sample and the acquisition temperature, and is between 128 and 1700 scans. The temperature of the sample is balanced for 30 min before the start of the acquisition. Lorentzian noise is filtered over the entire spectral window before the Fourier transform on the top of the echo. Dipalmitoylphosphatidylcholine vesicles (DPPC) act as external reference in the NMR $^{31}$P. The deconvolution of the spectra was carried out with the TOPSPIN software and dmfit-2009 (Massiot D, Fayon F, Capron M, King I, Le Calvé S, Alonso B, et al. *Magn. Reson. Chem.*, 2002, 40, 70-76).

Results

FIG. 1 very clearly shows via NMR $^{31}$P at ambient temperature (Hahn echo sequence) that the unbranched compound (I-1) is self-organised into a hydrated medium in lamellar form while the unbranched compounds of the invention (branching obtained by a reaction of the thiol-ene type; Compounds II-1, II-2, II-3, II-4) generate supramolecular aggregates adopting a hexagonal structure. The NMR $^{31}$P spectra, recorded under the same conditions, the co-formulation 1/1 (molar ratio) of the unbranched cationic compound I-1 and of the zwitterionic and branched co-lipid II-8, shows that the co-lipid leads to the formation of supramolecular aggregates of hexagonal structure. This structuring can therefore be induced by the presence in the co-formulation of a neutral lipid (zwitterionic) branched by thiol-ene reaction.

2) Measurement of the Size and of the Zeta Potential

Preparation of the Samples

The cationic lipids were formulated in a liposomal solution by the method of hydration of a lipid film. Initially, a fraction of a concentrated solution of the cationic lipid is placed in a glass tube and evaporated to give a thin lipid film. 1 mL of water is then added to the film and the film is hydrated for 3 days at 4° C. The solution is then vortexed (1 min) and placed under ultrasound (30 to 60 min) at 45 kHz. Then 150 μL of the liposomal solution is diluted in 1.5 mL of sterile water. After filtration (200 μm) of the liposomal solution, the size and the zeta potential of liposomes and lipoplexes are determined.

Conditions for Acquisition

The size and zeta potential (ξ) of the liposomes and of the lipoplexes were measured with a Zetasizer Nano ZS (Malvern Instruments) at 25° C. after a suitable dilution of the formulations. For the measurements of the lipoplexes, each test used 40 mg of plasmid DNA in water with the required amount of cationic lipid studied in order to form lipoplexes with charge ratios ranging from 0.5 to 8.0. For the measurements of the liposomes, a quantity of lipid equivalent to a mixture having a 1.0 charge ratio in water was used.

Results

| Compound | Size (nm) | PdI | Zeta Potential (mV) | ΔPZ (mV) |
|---|---|---|---|---|
| I-1 | 94 | 0.26 | +54 | 4 |
| II-1 | 99 | 0.26 | +33 | 7 |
| II-2 | 148 | 0.15 | +37 | 5 |
| II-3 | 187 | 0.36 | +44 | 5 |
| II-4 | 137 | 0.19 | +50 | 7 |
| II-8 + I-1 (1/1) | 136 | 0.2 | +48 | 6 |
| II-5 | 230 | 0.30 | +24 | 6 |
| II-6 | 188 | 0.30 | +58 | 7 |
| II-7 | 132 | 0.20 | +53 | 8 |

This size data shows that the supramolecular aggregates formed according to the method of hydration of a lipid film followed by a sonication step, have very usual sizes between 90 and 230 nm. Polydispersity indices (PdI) reflect the relatively homogeneous nature of these sizes in the samples. The zeta potential of these samples, which is always positive, corresponds to the usual values for cationic amphiphilics or co-formulations comprising at least one cationic amphiphilic.

Biological Study

Materials

Cells and Culture Conditions.

The C2C12 cell line is used as an example; it is immortalised mouse myoblasts. These cells are cultured in DMEM medium (Lonza) supplemented with decomplemented serum (10%), L-Glutamine (2 mM) and penicillin (100 U/mL)+streptomycin (100 μg/mL). The cells are maintained in an incubator at 37° C. in a humid atmosphere and 5% $CO_2$.

Plasmid DNA.

The luciferase plasmid reporter pEGFP-Luc (Clontech) is used in these tests.

Methods Formation of Lipoplexes.

The lipoplexes are prepared in OptiMEM (Gibco) by mixing different amounts of a given compound of the invention with 5 μg of DNA, in order to form lipoplexes [lipid/DNA] characterised by charge ratios (+/−) between 0.5 and 8.0.

Condensation of DNA.

Ethidium bromide is inserted into the DNA before being mixed with the compounds to be tested. The DNA condensation is then evaluated by agarose gel electrophoresis. DNA alone (not complexed) is used as a reference.

Transfection In Vitro.

The compounds are tested in transient transfection of cultured cells in vitro. The protocol used is one that has been described previously in several scientific publications (Felgner P. L. et al., *Proc. Natl. Acad. Sci. U.S.A.* 1987, 84, 7413-7417; Le Gall T. et al., *J. Med. Chem.* 2010, 53, 1496-1508). Briefly, 24 hours before the actual transfection, the cells are seeded in 96-well plates at a density of 12,500 cells per well. The complexes [lipid/DNA] are deposited directly into the cell culture medium at a rate of 0.25 μg of DNA per well. After approximately 36 h of incubation, the culture medium is removed and cells are lysed with 75 μL of Passive Lysis Buffer (Promega) 0.5× per well. After 24 h of storage at −20° C., each lysate is used to assay the total protein, measure the luciferase activity and conduct a cell viability test.

Transfection Efficiency.

The luciferase activity is determined with the Luciferase Assay System kit (Promega). Total proteins are quantified using a BCA assay (Interchim) colorimetric test. The transfection efficiency is calculated by dividing the luciferase activity by the quantity of total proteins; it is expressed as relative light units per mg protein (RLU/mg).

Cell Viability.

Cell viability is assessed using the Vialight kit (Lonza). Control cells (untreated) are used as reference (100% viability).

Results

The capacity of compounds to condense DNA is evaluated using the fluorescence properties of the latter when incubated in the presence of ethidium bromide. The condensation of DNA is accompanied by exclusion of the inserted ethidium bromide. The reduction in the fluorescence that results as such provides information on the degree of compaction of the DNA obtained thanks to a given compound.

Figure 2:
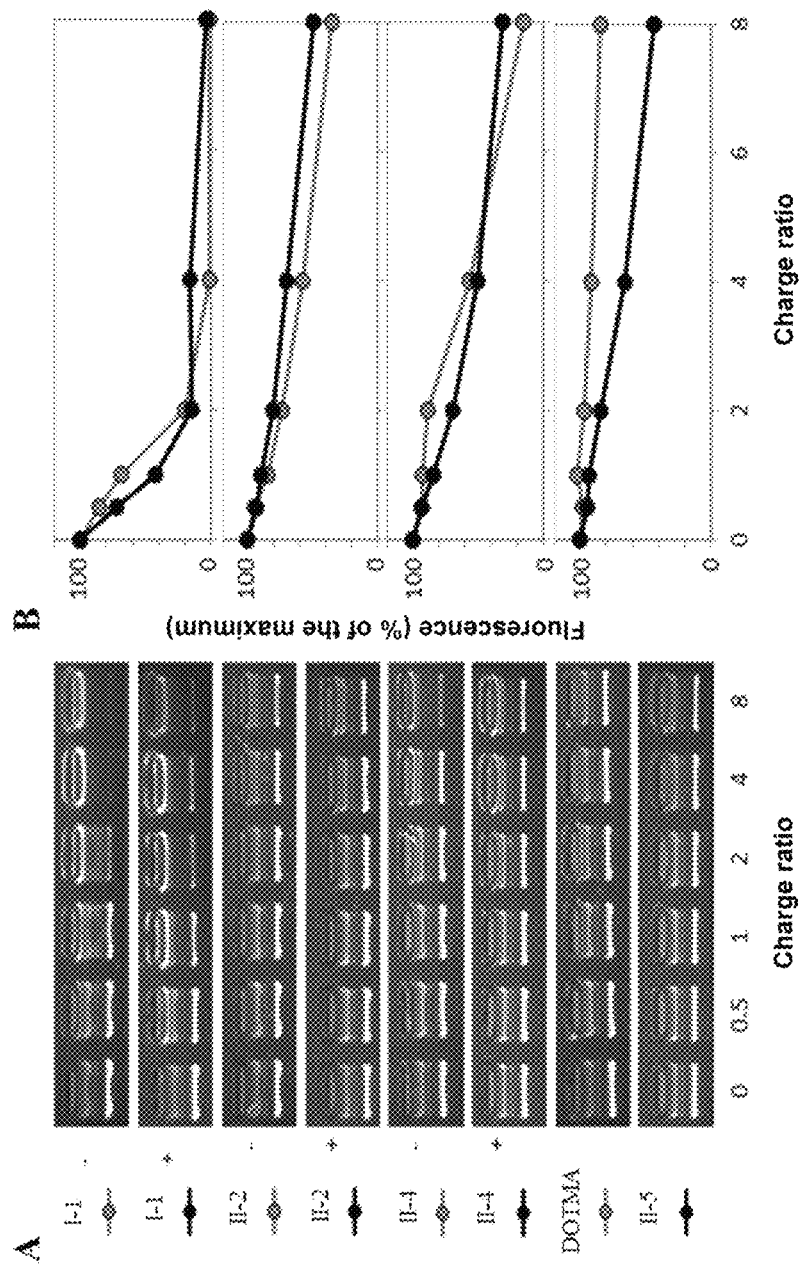
FIG. 2 relates to the evaluation of the condensation of DNA by the various compounds of the invention, and formulated either alone (−) or with DOPE (+). A is an agarose gel 1% after migration (0.1 μg of DNA per well; B is a graph showing the fluorescence of the low band of DNA in relation to the charge ratio. The fluorescence of the low band of DNA was quantified then expressed as a percentage of the maximum fluorescence, measured for non-complexed naked DNA.

FIG. 2 shows that the branched compounds of the invention compact the DNA but less complete than the unbranched compounds (I-1).

Figure 3:
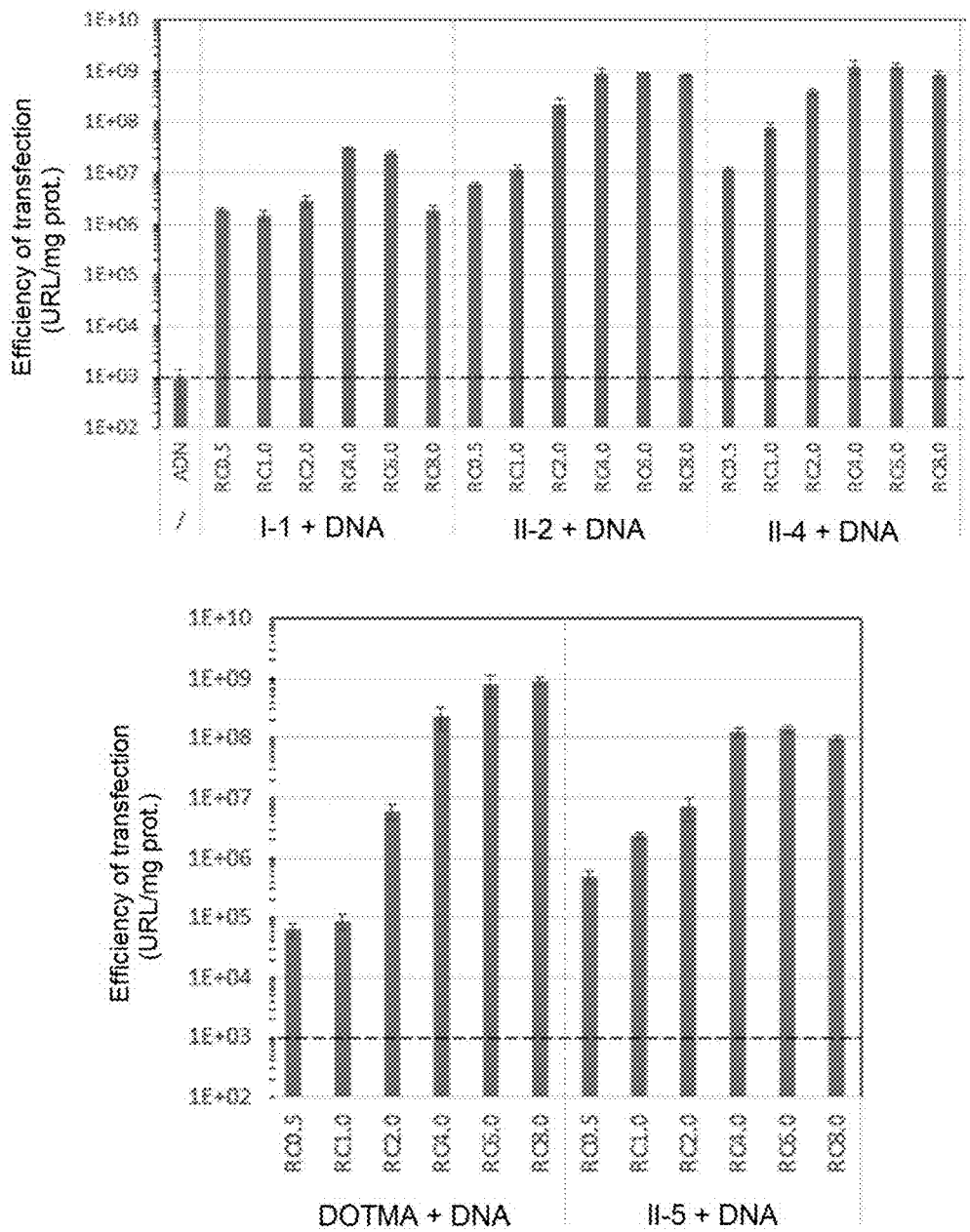
FIG. 3 is a bar graph showing the transfection effectiveness in vitro of cells C2C12 by means of compounds of the invention and controls the compound I-1 and DOTMA. The threshold for positivity (dashed line) is determined with non-transfected cells (exposed to non-complexed naked DNA; "DNA"). CR, charge ratio.

The lipoplexes are then used in vitro cell transfection. FIG. 3 shows the results obtained by in vitro transfection of C2C12 cells using lipoplexes formed from different branched cationic amphiphilic lipids according to the invention (II-2, II-4 and II-5) or unbranched cationic amphiphilic lipids such as I-1 or DOTMA.

Figure 4:
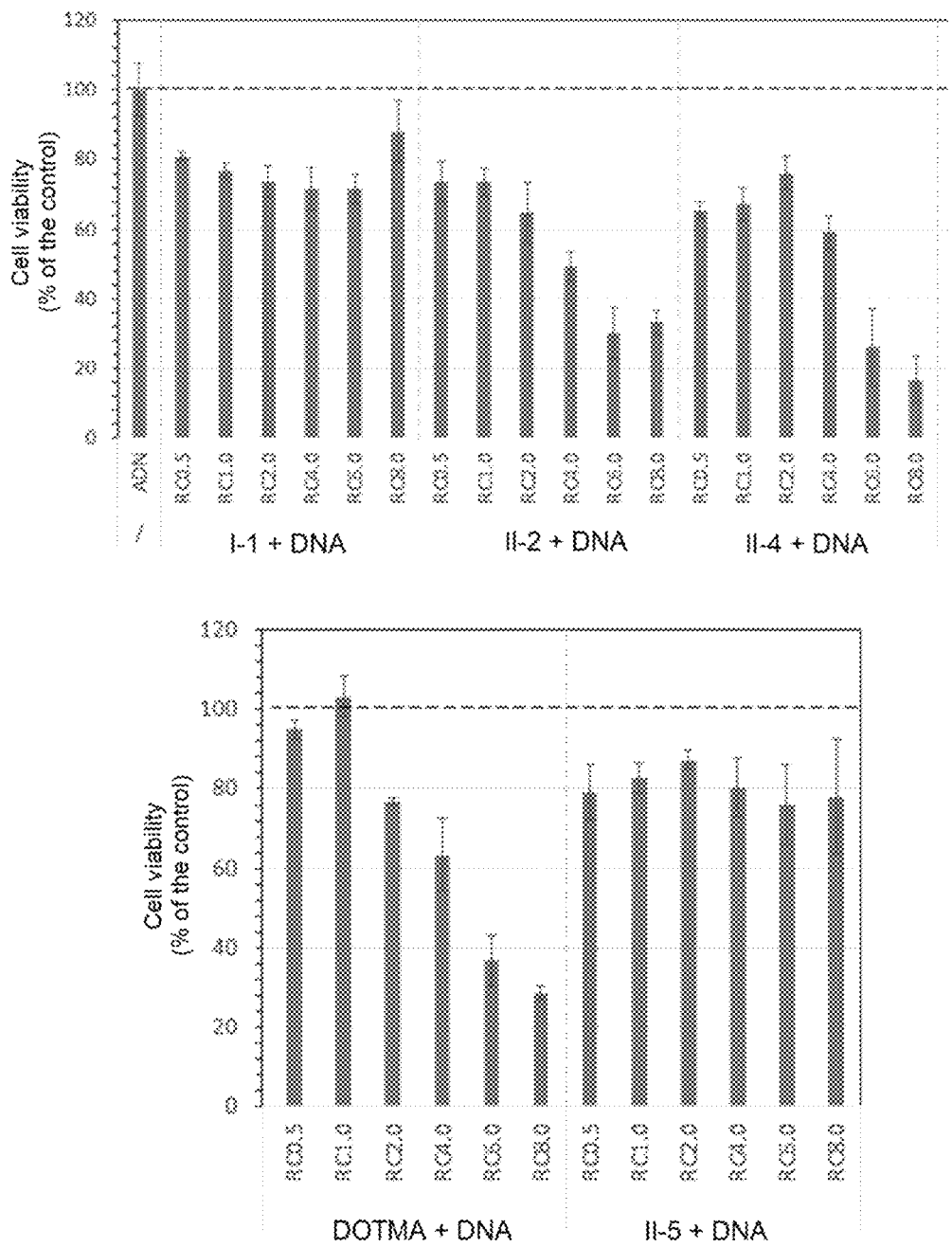
FIG. 4 is a bar graph showing the viability of C2C12 cells after transfection in vitro by means of compounds of the invention and controls the compound I-1 and DOTMA. The viability of non-transfected cells (exposed to non-complexed naked DNA; "DNA") is used as a reference (value 100%, dashed lines). CR, charge ratio.

All of the compounds tested are effective for delivering plasmid DNA inside C2C12 cells, cells known to be relatively difficult to transfect. However, compared to the compound with linear fatty chains I-1, compounds with branched fatty chains II-2 and II-4 make it possible to obtain significantly higher transfection efficiencies, with a gain of up to 40 times the reference (FIG. 3). Furthermore, these higher efficiencies are obtained while maintaining good cell viability as shown in FIG. 4.

Figure 5:
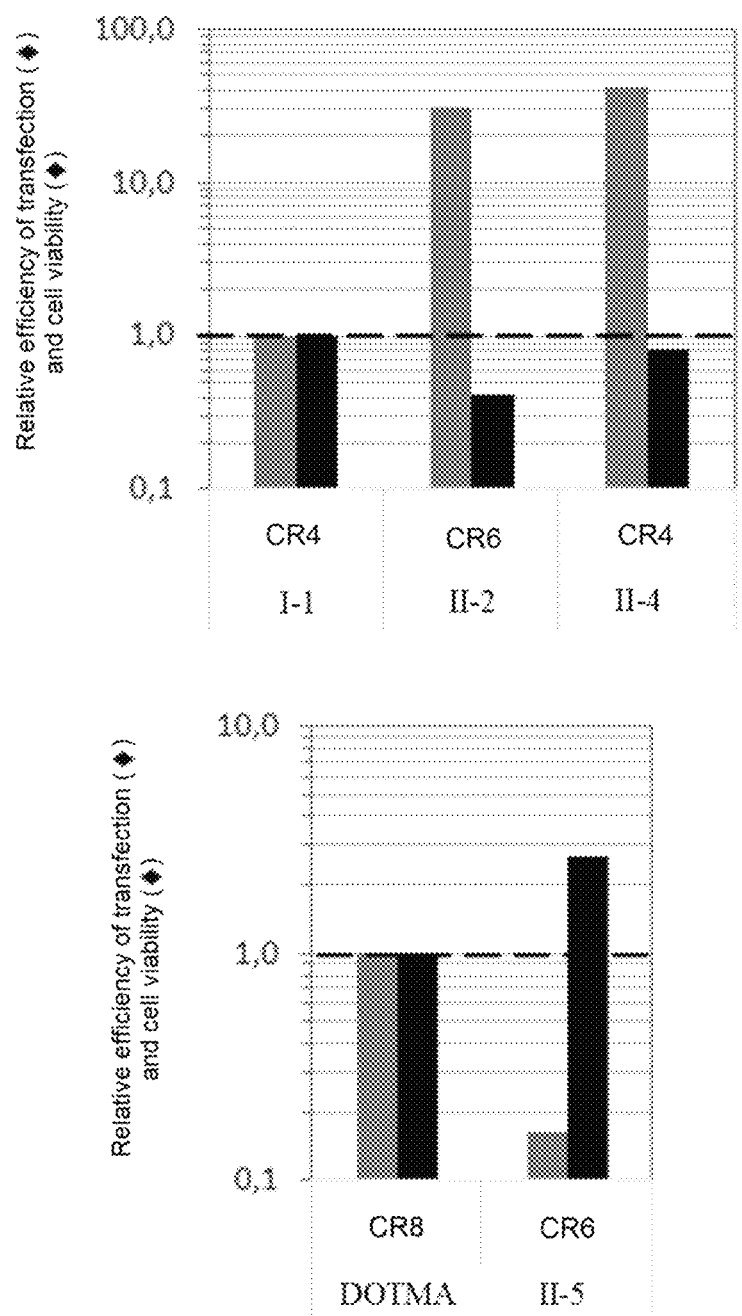
FIG. 5 is a bar graph showing the transfection effectiveness and cell viability of compounds with branched fatty chains expressed in relation to cells obtained with the compound with linear fatty chains. For each compound, the values considered were those obtained at the charge ratio for which the peak in effectiveness was reached.

Compared to DOTMA, the derivative with branched fatty chains II-5 reaches lower transfection efficiencies but it makes it possible to maintain good cell viability, even at high charge ratio (FIG. 5).

These results indicate that a branching of the fatty chains of the cationic lips can make it possible to increase the transfecting power and/or to improve the biocompatibility, i.e. reduce its toxicity, according to the starting cationic lipid and the branching introduced.

The invention claimed is:

1. An amphiphilic compound of general formula (II):

$$\begin{bmatrix} CH_3-(CH_2)_n-CH-CH-(CH_2)_m-CH-CH-(CH_2)_p-(CH_2)_q-L_1 \\ \quad\quad\quad\quad\quad R_1\;\; R_2 \quad\quad\quad R_2\;\; R_1 \\ CH_3-(CH_2)_{n'}-CH-CH-(CH_2)_{m'}-CH-CH-(CH_2)_{p'}-(CH_2)_{q'}-L_2 \\ \quad\quad\quad\quad\quad R_3\;\; R_4 \quad\quad\quad R_4\;\; R_3 \end{bmatrix}_a L_3-Z \quad (II)$$

wherein:

$L_1$ and $L_2$ are each independently a linker selected from the group consisting of a single bond and alkyl;

$L_3$ is a linker selected from the group consisting of alkylphosphoramidates and alkyloxy;

Z is a polar functional group, said group being cationic, anionic, zwitterionic or neutral;

a is 1;

n, n', q and q' are each independently an integer from 1 to 15;

m, m', p and p' are each independently an integer from 0 to 4 with the condition that:

at least one of m and p is different from 0; and at least one of m' and p' is different from 0;

$R_1$ and $R_2$ are one a hydrogen and the other a thioether group of formula —S-$L_4$-$R_5$ and $R_3$ and $R_4$ are one a hydrogen and the other a thioether group of formula —S-$L_4$-$R_5$ wherein:

$L_4$ is a linker selected from the group consisting of a single bond, alkyl, cycloalkyl and alkylaryl; and $R_5$ is a hydrogen atom, or:

polar group selected from the group consisting of organic salts of the ammonium, phosphonium, and imidazolium type and protonable neutral heterocycles;

a reactive group selected from the group consisting of group $N_3$, amino, alkylamino, COOH, amide, maleimide, alkyne, SH, OH, ester, activated ester, activated carboxylic acid, halo, nitro, nitrile, isonitrile, acrylamide, aldehyde, ketone, acetals, ketals, anhydride, thiocyanate, isothiocyanate, isocyanate, hydrazine, hydrazides, hydrazones, ethers, oxides, cyanates, diazo, diazonium, sulphides, disulphides, sulphoxides, sulphones, sulphonic acids, sulphinic acids, sulphates, sulphenic acids, amidines, imides, imines, imidates, nitrones, hydroxylamines, oximes, hydroxamic acids, thiohydroxamic acids, allenes, ortho esters, sulphites, enamines, ynamines, ureas, pseudo-ureas, semicarbazides, carbodiimides, and carbamates; or a bioactive group selected from the group consisting of amino acids, peptides, proteins, antibodies, enzymes, polysaccharides, nucleosides, nucleotides, oligonucleotides, fluorophores, chromophores, radioisotopes, carboranes.

2. The compound according to claim 1, of formula (IIa):

$$\text{(IIa)}$$

$$CH_3-(CH_2)_n-\underset{R_1}{\overset{R_1}{CH}}-\underset{R_2}{\overset{R_2}{CH}}-(CH_2)_m-\underset{R_2}{\overset{R_2}{CH}}-\underset{R_1}{\overset{R_1}{CH}}-(CH_2)_p-(CH_2)_q-O-\overset{O}{\underset{\|}{P}}$$

$$CH_3-(CH_2)_{n'}-\underset{R_3}{\overset{R_3}{CH}}-\underset{R_4}{\overset{R_4}{CH}}-(CH_2)_{m'}-\underset{R_4}{\overset{R_4}{CH}}-\underset{R_3}{\overset{R_3}{CH}}-(CH_2)_{p'}-(CH_2)_{q'}-O\quad N-(CH_2)_r-Z$$
$$\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad R_6$$

wherein $R_1$, $R_2$, $R_3$, $R_4$, Z, n, n', m, m', p, p', q and q' are as defined in claim 1;
$R_6$ is a hydrogen or an alkyl; and
r is an integer from 1 to 10.
3. The compound according to claim 1, of formula (IIb):
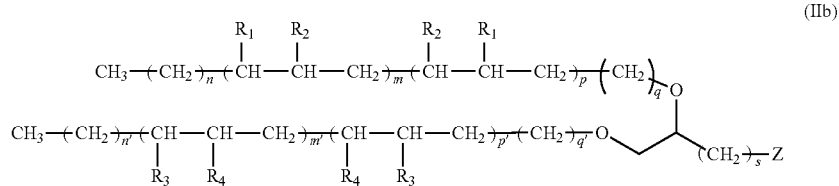
wherein $R_1$, $R_2$, $R_3$, $R_4$, Z, n, n', m, m', p, p', q and q' are as defined in claim 1; and
s is an integer from 1 to 10.
4. The compound according to claim 1, selected from the group consisting of:
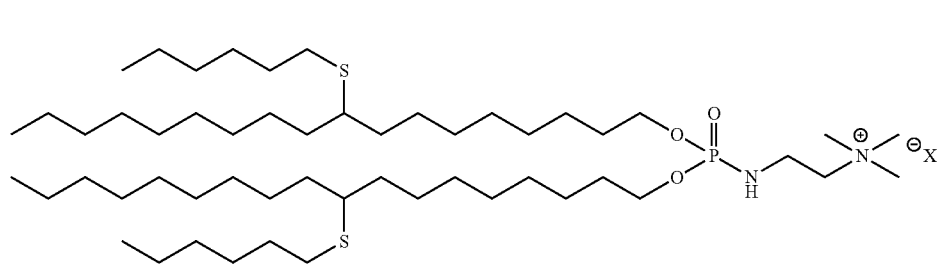
II-1a
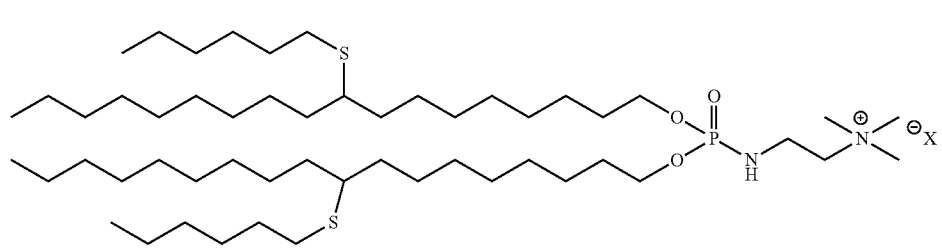
II-1b
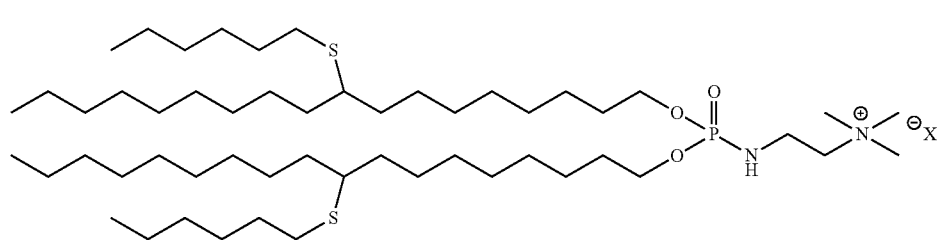
II-1c
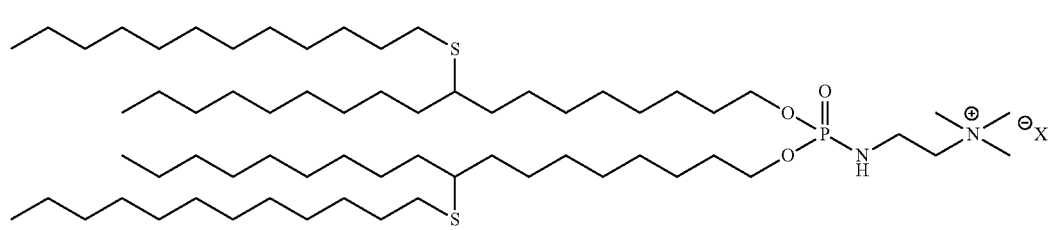
II-2a

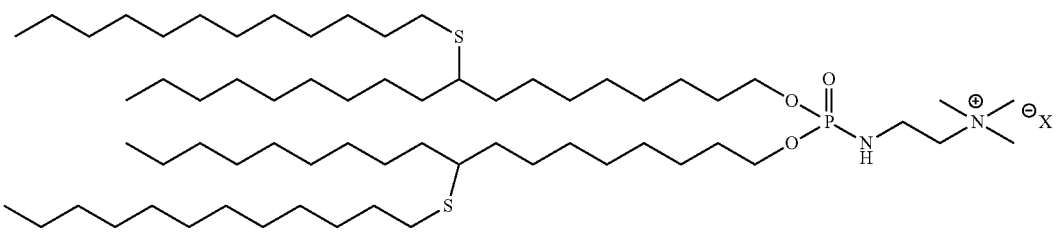
II-2b
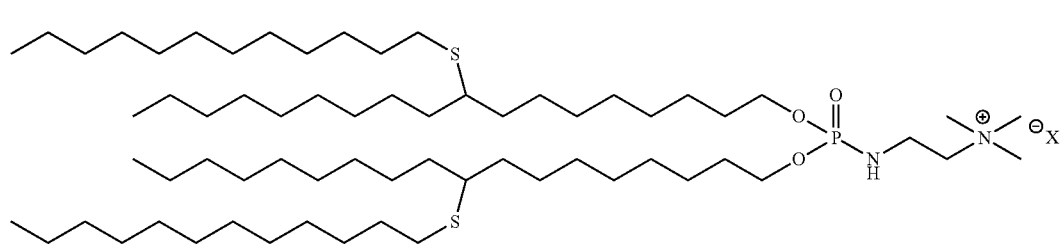
II-2c
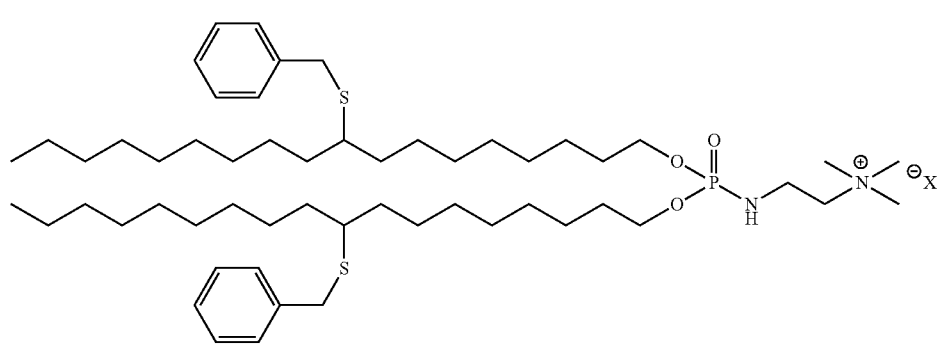
II-3a
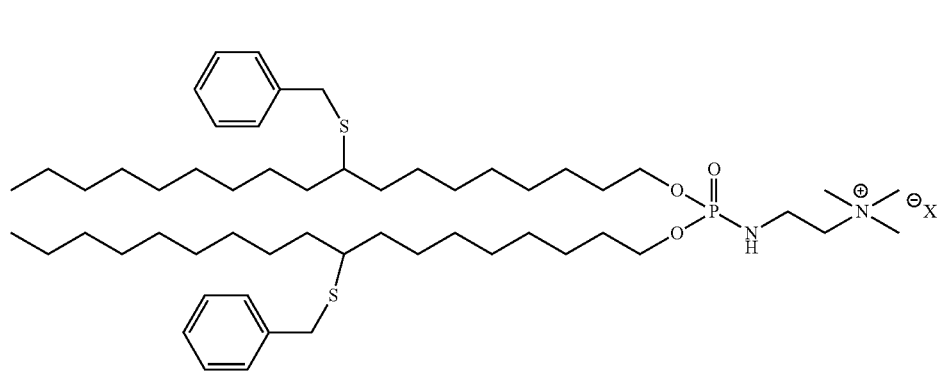
II-3b
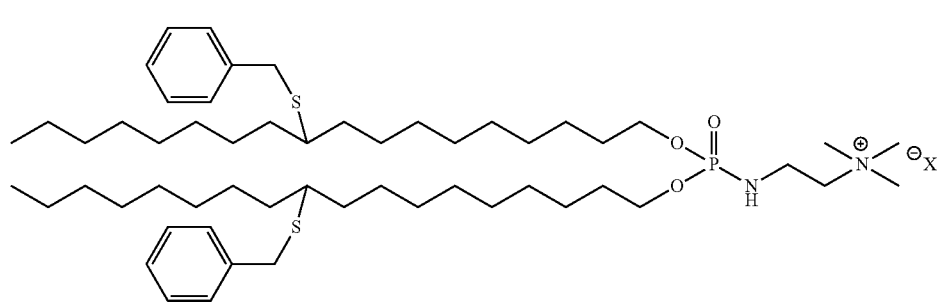
II-3c II-4a
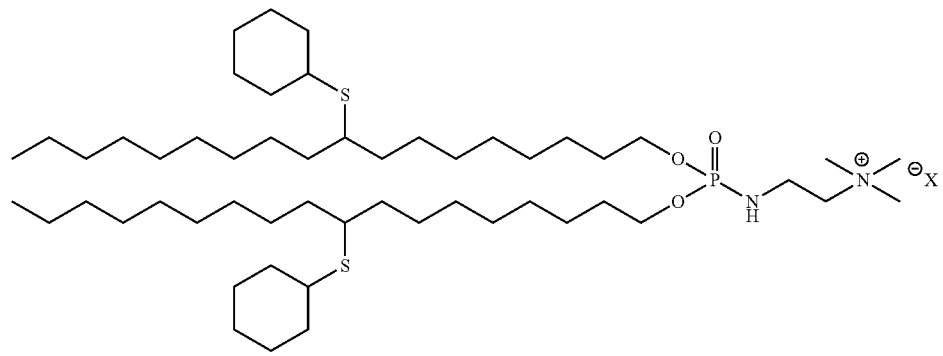
II-4b
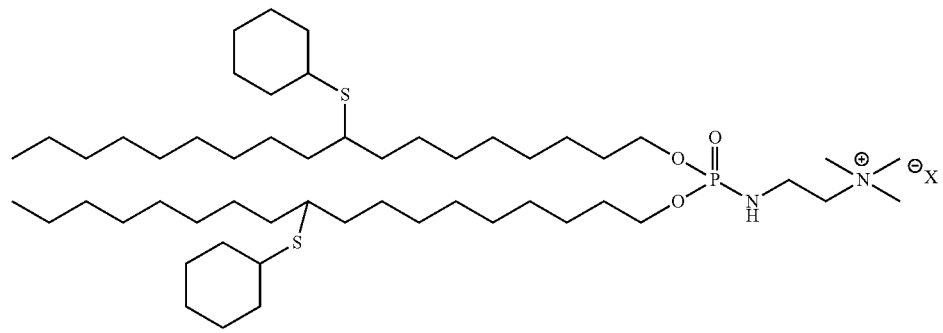
II-4c
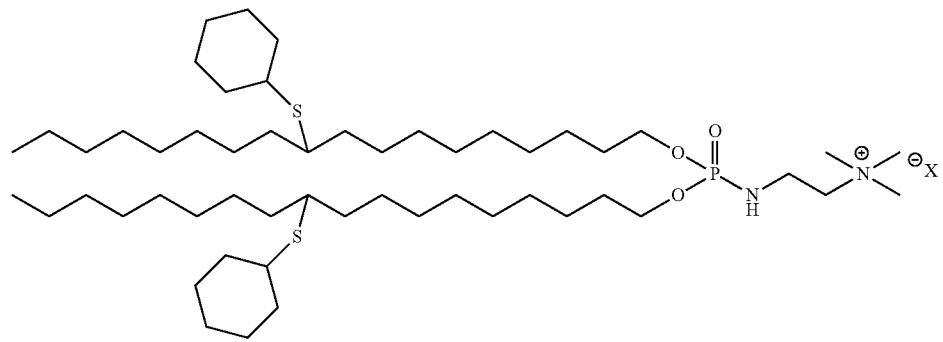
II-5a
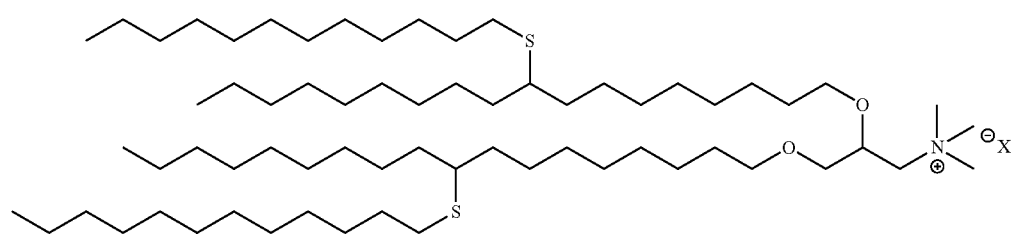
II-5b
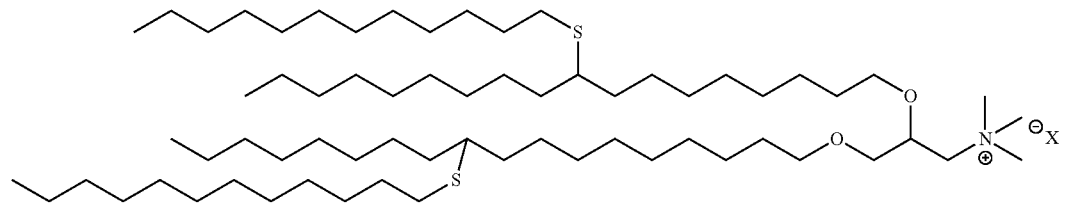

-continued
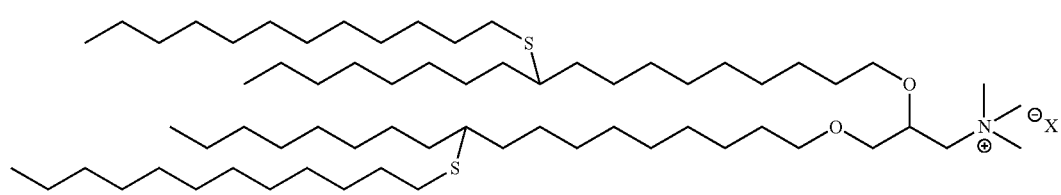
II-5c
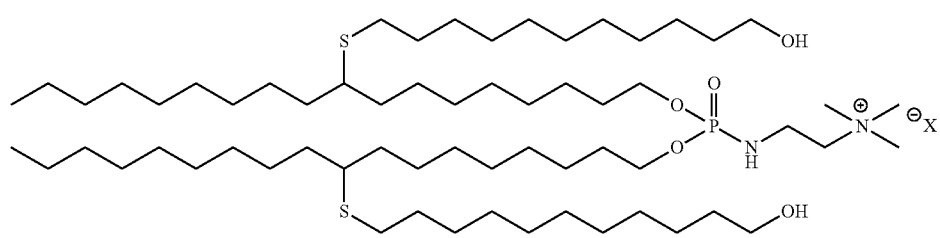
II-6a
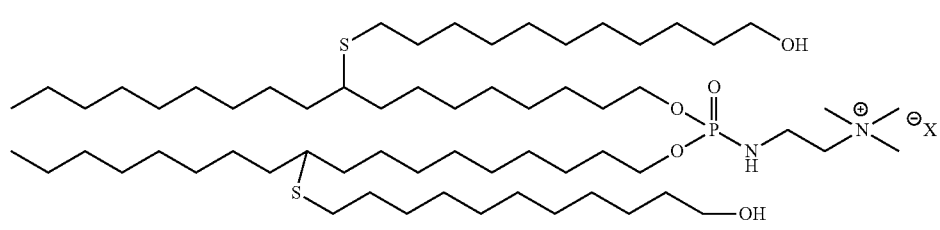
II-6b
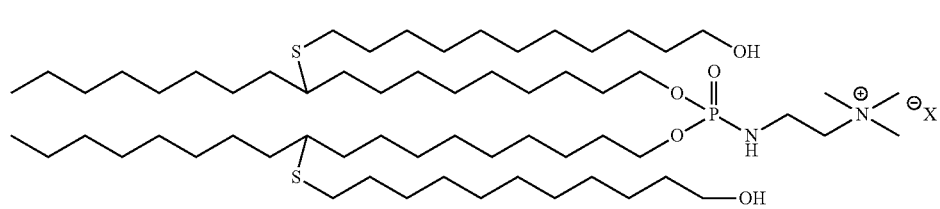
II-6c
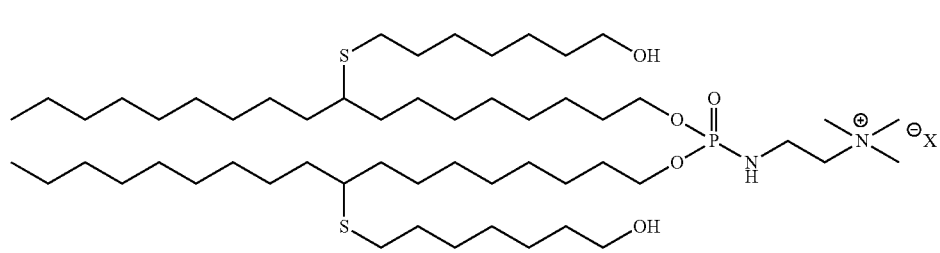
II-7a
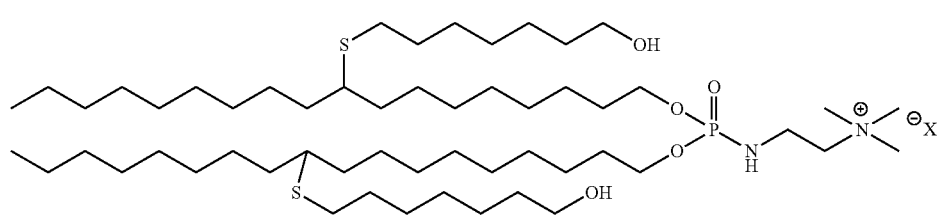
II-7b
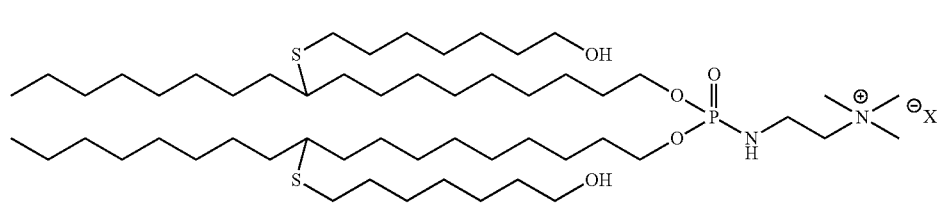
II-7c -continued
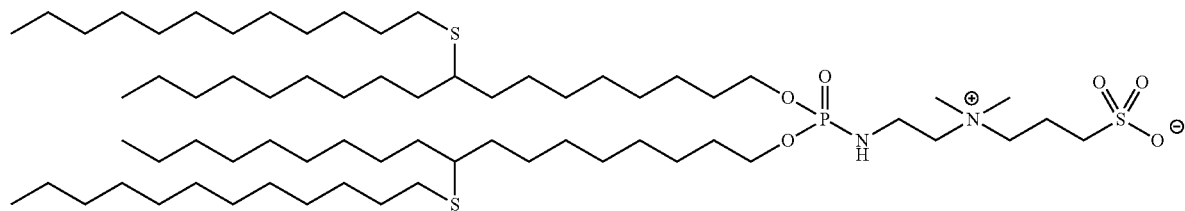
II-8a
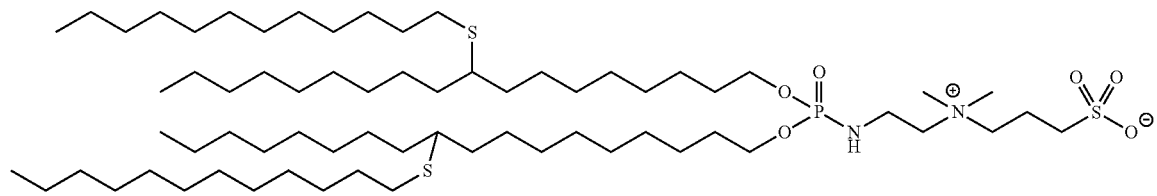
II-8b
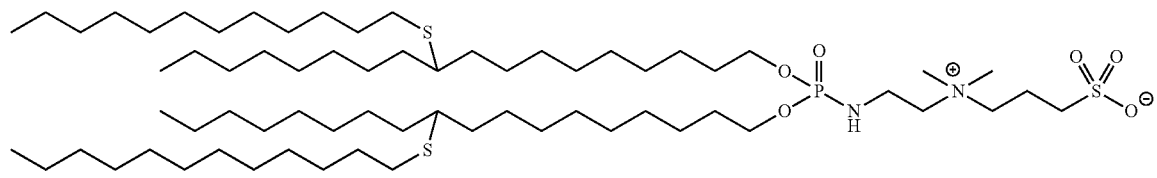
II-8c
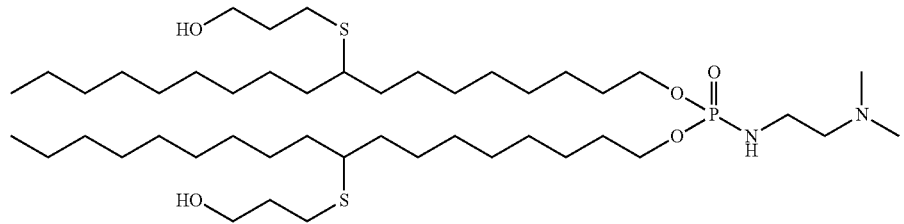 [SMILES: CCCCCCCCCC(CCCCCCCCOP(=O)(NCCN(C)C)OCCCCCCCCC(CCCCCCCCC)SCCCO)SCCCO]
II-9a
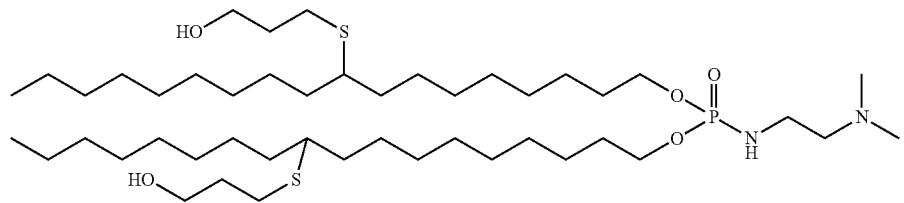 [SMILES: CCCCCCCCCC(CCCCCCCCOP(=O)(NCCN(C)C)OCCCCCCCCCC(CCCCCCCC)SCCCO)SCCCO]
II-9b
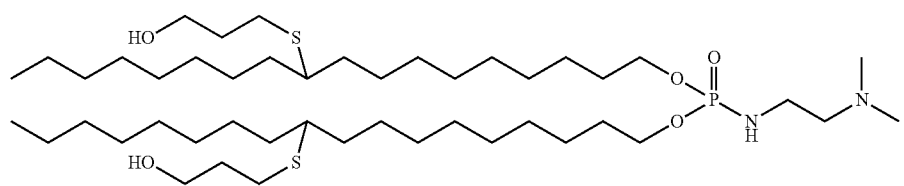 [SMILES: CCCCCCCCC(CCCCCCCCCOP(=O)(NCCN(C)C)OCCCCCCCCCC(CCCCCCCC)SCCCO)SCCCO]
II-9c II-10a
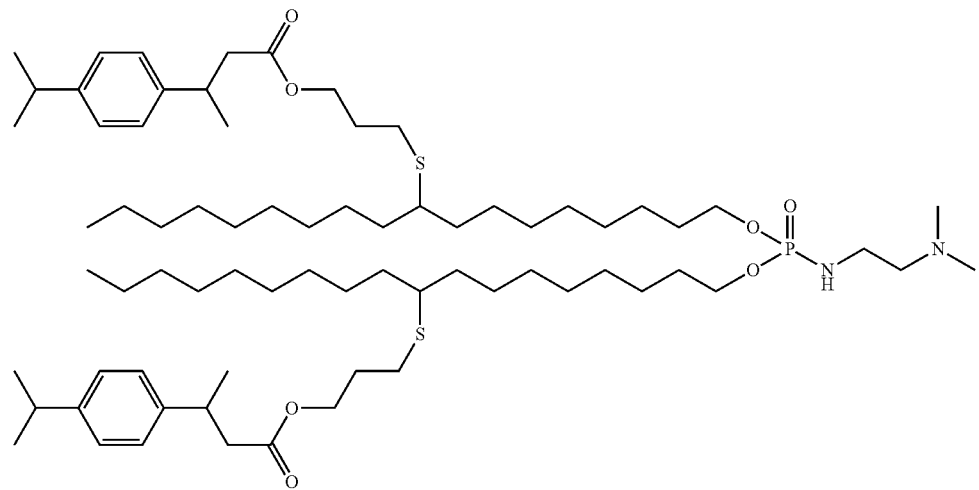 [SMILES: CCCCCCCCCC(CCCCCCCCOP(=O)(NCCN(C)C)OCCCCCCCCC(CCCCCCCCC)SCCCOC(=O)CC(C)c1ccc(C(C)C)cc1)SCCCOC(=O)CC(C)c1ccc(C(C)C)cc1]
II-10b
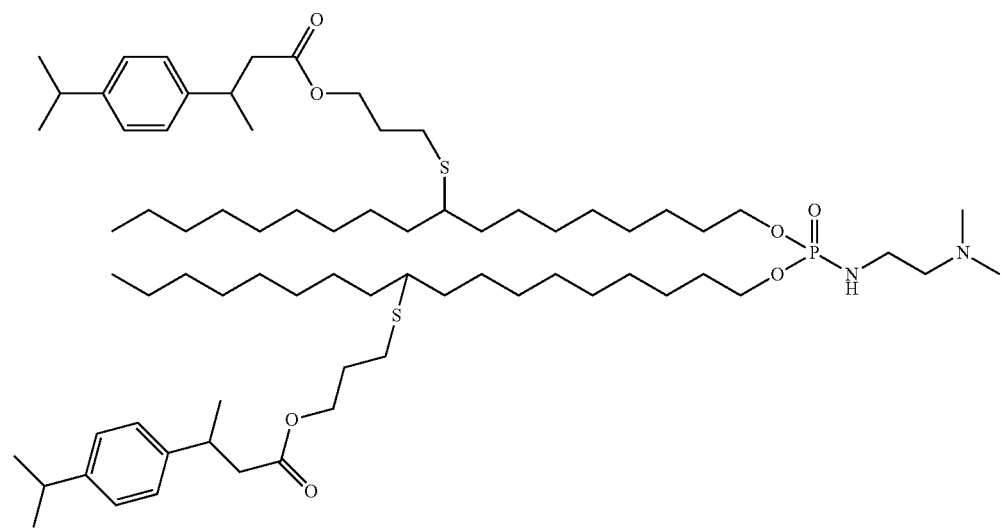 [SMILES: CCCCCCCCCC(CCCCCCCCOP(=O)(NCCN(C)C)OCCCCCCCCCC(CCCCCCCC)SCCCOC(=O)CC(C)c1ccc(C(C)C)cc1)SCCCOC(=O)CC(C)c1ccc(C(C)C)cc1]
and
II-10c
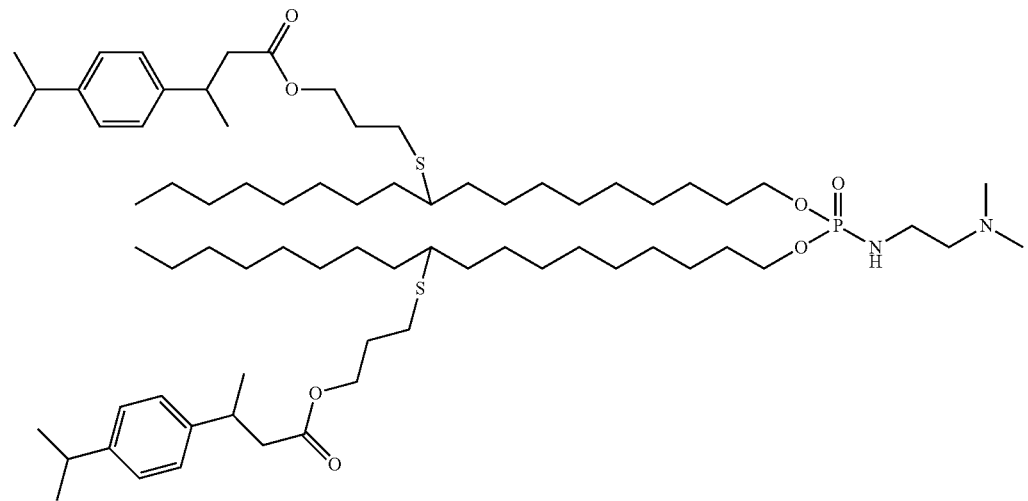

wherein X⁻ is a counterion.

5. A liposome comprising at least one of the compounds according to claim 1 having a hexagonal phase.

6. A lipoplex comprising at least one of the compounds according to claim 1 having a hexagonal phase.

7. A pharmaceutical composition comprising a compound according to claim 1 and a physiologically acceptable vehicle.

8. A pharmaceutical composition comprising a liposome according to claim 5 and a physiologically acceptable vehicle.

9. A pharmaceutical composition comprising a lipoplex according to claim 6 and a physiologically acceptable vehicle.

* * * * *